(12) United States Patent
Tanabe et al.

(10) Patent No.: US 11,016,026 B2
(45) Date of Patent: May 25, 2021

(54) OPTICAL ANALYSIS METHOD AND OPTICAL ANALYSIS DEVICE USING SINGLE LIGHT-EMITTING PARTICLE DETECTION

(71) Applicant: OLYMPUS CORPORATION, Tokyo (JP)

(72) Inventors: Tetsuya Tanabe, Tokyo (JP); Takuya Hanashi, Mitaka (JP); Hidetaka Nakata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 275 days.

(21) Appl. No.: 15/983,412

(22) Filed: May 18, 2018

(65) Prior Publication Data

US 2018/0259457 A1 Sep. 13, 2018

Related U.S. Application Data

(63) Continuation of application No. PCT/JP2015/084490, filed on Dec. 9, 2015.

(51) Int. Cl.
*G01N 21/64* (2006.01)
*C12Q 1/6816* (2018.01)
*G01N 21/78* (2006.01)

(52) U.S. Cl.
CPC ....... *G01N 21/6428* (2013.01); *C12Q 1/6816* (2013.01); *G01N 21/64* (2013.01);
(Continued)

(58) Field of Classification Search
CPC .... G01N 21/6428; G01N 21/64; G01N 21/78; G01N 21/6458; G01N 21/6408;
(Continued)

(56) References Cited

U.S. PATENT DOCUMENTS

| 4,251,733 A | 2/1981 | Hirleman, Jr. |
| 4,885,473 A | 12/1989 | Shofner et al. |

(Continued)

FOREIGN PATENT DOCUMENTS

| CN | 101946180 A | 1/2011 |
| EP | 1 906 172 A1 | 4/2008 |

(Continued)

OTHER PUBLICATIONS

WO2012014778 description in English, downloaded Jun. 7, 2020 from https://worldwide.espacenet.com/publicationDetails/description?CC=JP&NR=WO2012014778A1&KC=A1&FT=D&ND=3&date=20130912&DB=EPODOC&locale=en_EP#, 40 pp. (Year: 2020).*

(Continued)

*Primary Examiner* — Daniel L Murphy
(74) *Attorney, Agent, or Firm* — Westerman, Hatton, Daniels & Adrian, LLP

(57) ABSTRACT

In the scanning molecule counting method of measuring light intensity from a light detection region while moving the position of the light detection region of a confocal or multiphoton microscope in a sample solution containing light-emitting particles, generating time series light intensity data and detecting each of signals of the light-emitting particles individually in the data, wherein the light-emitting particles are formed by binding to a particle to be observed a light-emitting probe which emits light through binding to the particle to be observed and in which a stochastic transition between a non-light-emitting state and a light-emitting state occurs in the unbound state, the moving speed of the position of the light detection region is adjusted to make the time during which the unbound probe is encompassed by the moving light detection region longer than an average lifetime during which the probe is in the light-emitting state.

9 Claims, 6 Drawing Sheets

Figure 2A:
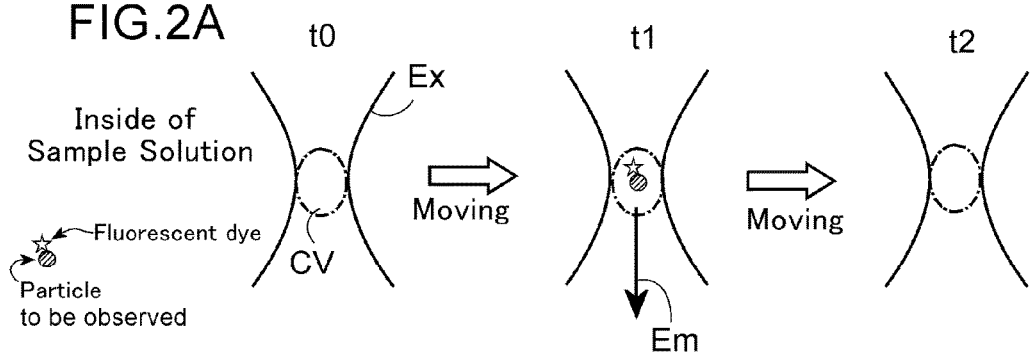

Specification includes a Sequence Listing.

(52) U.S. Cl.
CPC ......... *G01N 21/6458* (2013.01); *G01N 21/78* (2013.01); *G01N 21/6408* (2013.01); *G01N 2021/6439* (2013.01)

(58) Field of Classification Search
CPC .......... G01N 2021/6439; C12Q 1/6816; C12Q 2565/101; C12Q 2565/601
USPC ...................................................... 356/3.02
See application file for complete search history.

(56) References Cited

U.S. PATENT DOCUMENTS

| | | | |
|---|---|---|---|
| 4,979,824 | A | 12/1990 | Mathies et al. |
| 5,319,575 | A | 6/1994 | Lilienfeld |
| 5,866,336 | A | 2/1999 | Nazarenko et al. |
| 5,900,933 | A | 5/1999 | Schwartz et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,449,042 | B1 | 9/2002 | Hamann |
| 6,563,583 | B2 | 5/2003 | Ortyn et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,174,692 | B2 * | 5/2012 | Hell ........................ G02B 27/58 356/317 |
| 8,284,484 | B2 | 10/2012 | Hoult et al. |
| 9,068,944 | B2 | 6/2015 | Tanabe |
| 9,470,680 | B2 * | 10/2016 | Gonzalez, Jr. ........ G01N 33/542 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sambas |
| 2004/0022684 | A1 | 2/2004 | Heinze et al. |
| 2004/0036870 | A1 | 2/2004 | Goix |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2007/0250274 | A1 | 10/2007 | Volkov et al. |
| 2008/0052009 | A1 | 2/2008 | Chiu et al. |
| 2008/0156999 | A1 | 7/2008 | Nishiwaki et al. |
| 2008/0158561 | A1 | 7/2008 | Vacca et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2011/0001969 | A1 | 1/2011 | Ishii et al. |
| 2011/0192595 | A1 | 8/2011 | Ronaes et al. |
| 2013/0122488 | A1 | 5/2013 | Tanabe et al. |
| 2013/0228705 | A1 | 9/2013 | Nishikawa et al. |
| 2013/0228706 | A1 | 9/2013 | Yamaguchi et al. |
| 2013/0242307 | A1 | 9/2013 | Hanashi et al. |
| 2014/0099630 | A1 | 4/2014 | Nakata |
| 2014/0134608 | A1 | 5/2014 | Hanashi et al. |
| 2014/0162268 | A1 | 6/2014 | Tanabe et al. |

FOREIGN PATENT DOCUMENTS

| | | | |
|---|---|---|---|
| EP | 2 752 655 | A1 | 7/2014 |
| EP | 2 840 380 | A1 | 2/2015 |
| JP | 63-225145 | A | 9/1988 |
| JP | 4-337446 | A | 11/1992 |
| JP | 2002-507762 | A | 3/2002 |
| JP | 2002-543414 | A | 12/2002 |
| JP | 2004-506192 | A | 2/2004 |
| JP | 2005-98876 | A | 4/2005 |
| JP | 2005-99662 | A | 4/2005 |
| JP | 2007-20565 | A | 2/2007 |
| JP | 4023523 | B2 | 12/2007 |
| JP | 2008-116440 | A | 5/2008 |
| JP | 2008-536093 | A | 9/2008 |
| JP | 2008-292371 | A | 12/2008 |
| JP | 2009-145242 | A | 7/2009 |
| JP | 2009-281831 | A | 12/2009 |
| JP | 2009-288161 | A | 12/2009 |
| JP | 2010-190730 | A | 9/2010 |
| JP | 2011-2415 | A | 1/2011 |
| JP | 2011-508219 | A | 3/2011 |
| WO | 1998/016814 | A1 | 4/1998 |
| WO | 1999/047963 | A1 | 9/1999 |
| WO | 00/71991 | A1 | 11/2000 |
| WO | 2000/066985 | A1 | 11/2000 |
| WO | 2002/012864 | A1 | 2/2002 |
| WO | 2006/084283 | A2 | 8/2006 |
| WO | 2007/010803 | A1 | 1/2007 |
| WO | 2007/118209 | A2 | 10/2007 |
| WO | 2007/147159 | A2 | 12/2007 |
| WO | 2008/007580 | A1 | 1/2008 |
| WO | 2008/080417 | A1 | 7/2008 |
| WO | 2009/117033 | A2 | 9/2009 |
| WO | 2011/108369 | A1 | 9/2011 |
| WO | 2011/108370 | A1 | 9/2011 |
| WO | 2011/108371 | A1 | 9/2011 |
| WO | 2012/014778 | A1 | 2/2012 |
| WO | 2012/050011 | A1 | 4/2012 |
| WO | 2012/144528 | A1 | 10/2012 |
| WO | 2013/024650 | A1 | 2/2013 |

OTHER PUBLICATIONS

IPRP for PCT_JP2011_053482 English, 6 pp., Sep. 1, 2012 (Year: 2012).*

Office Action dated Sep. 3, 2019, issued in counterpart JP Application No. 2017-554710, with English translation. (7 pages).

Chinese Office Action dated Jan. 25, 2016, issued in related Chinese application No. 201280005999. 8.; with English translation (22 pages).

Chinese Office Action dated Aug. 2, 2016, issued in related Chinese application No. 201280005999. 8.; with English translation (10 pages).

Chinese Office Action dated Feb. 17, 2017, issued in related Chinese application No. 201280005999. 8.; with English translation (19 pages).

Chinese Office Action dated Apr. 24, 2015, issued in related Chinese application No. 201280041770.X; with English translation (27 pages).

Chinese Office Action dated Mar. 25, 2015, issued in related Chinese application No. 201280039905.9, with English translation (34 pages).

Europe Official Action dated Nov. 24, 2016, issued in related EP application No. 12823870.6. (9 pages).

Extended European search report dated Mar. 28, 2013, issued in related EP application No. 11750481.1 (6 pages).

Extended European Search Report dated Oct. 20. 2014. issued in related EP application No. 12770835.2 (10 pages).

Extended European Search Report dated Mar. 31, 2015, issued in related EP application No. 12823870.6 (15 pages).

Extended European Search Report dated Apr. 10, 2015, issued in related EP application No. 12827023.8 (13 pages).

Extended European Search Report dated Sep. 29, 2017, issued in related EP patent application No. 11750483.7. (11 pages).

Extended European Search Report dated Oct. 2, 2017, issued in related European application No. 11750482.9. (11 pages).

U.S. Advisory Action dated Feb. 14, 2018, issued in related U.S. Appl. No. 14/188,375 (8 pages).

Office Action dated Mar. 20, 2019, issued in related EP Application No. 11 750 482.9 (6 pages).

Non-Final Office Action dated Nov. 26, 2018, issued in U.S. Appl. No. 14/188,375. (36 pages).

(56) References Cited

OTHER PUBLICATIONS

International Search Report dated Mar. 29, 2011, issued in international application No. PCT/JP2011/053481 (counterpart of U.S. Appl. No. 13/596,243), w/English translation. (5 pages).
International Search Report dated Mar. 29, 2011, issued in international application No. PCT/JP2011/053482 (counterpart of U.S. Appl. No. 13/597,825), w/English translation. (5 pages).
International Search Report dated Mar. 29, 2011, issued in international application No. PCT/JP2011/053483 (counterpart of U.S. Appl. No. 13/596,280), w/English translation. (5 pages).
International Search Report dated Mar. 15, 2016, issued in international application No. PCT/JP2015/084490, w/English translation (counterpart of U.S. Appl. No. 15/983,412). (5 pages).
Written Opinion dated Mar. 29, 2011, issued in international application No. PCT/JP2011/053481 (counterpart of U.S. Appl. No. 13/596,243). (6 pages).
Written Opinion dated Mar. 29, 2011, issued in international application No. PCT/JP2011/053482 (counterpart of U.S. Appl. No. 13/597,825). (5 pages).
Written Opinion dated Mar. 29, 2011, issued in international application No. PCT/JP2011/053483 (counterpart of U.S. Appl. No. 13/596,280). (5 pages).
Written Opinion dated Mar. 15, 2016, issued in international application No. PCT/JP2015/084490(counterpart of U.S. Appl. No. 15/983,412). (4 pages).
International Preliminary Report on Patentability (PCT/IPEA/409) issued in international application No. PCT/JP2011/053481 (counterpart of U.S. Appl. No. 13/596,243) filed on Feb. 18, 2011, w/English translation. (17 pages).
International Preliminary Report on Patentability (PCT/IPEA/409) issued in international application No. PCT/JP2011/053482 (counterpart of U.S. Appl. No. 13/597,825) filed on Feb. 18, 2011, w/English translation. (17 pages).
International Preliminary Report on Patentability (PCT/IPEA/409) issued in international application No. PCT/JP2011/053483 (counterpart of U.S. Appl. No. 13/596,280) filed on Feb. 18, 2011, w/English translation. (17 pages).
U.S.Non-Final Office Action dated Apr. 2, 2013, issued in related U.S. Appl. No. 13/596,280. (13 pages).
U.S. Non-Final Office Action dated Jan. 3, 2013, issued in related U.S. Appl. No. 13/597,825. (10 pages).
U.S. Non-Final Office Action dated Oct. 4, 2013, issued in related U.S. Appl. No. 13/596,243. (15 pages).
Chinese Office Action dated Aug. 9, 2013, issued in related Chinese application No. 201180011640.7; with English translation. (16 pages).
Chinese Office Action dated Feb. 7, 2013, issued in related Chinese application No. 201180011644.5; with English translation. (18 pages).
Chinese Office Action dated Aug. 13, 2013, issued in related Chinese application No. 201180011655.3; with English translation. (16 pages).
Japanese Notice of Reasons-for-Rejection dated Dec. 18, 2012, issued in related JP application No. 2012-503060 with English translation. (6 pages).
Park et al. "Counting the Number of Fluorophores Labeled in Biomolecules by Observing the Fluorescence-Intensity Transient of a Single Molecule", Bulletin of the Chemical Society of Japan, dated Aug. 30, 2005, vol. 78, No. 9, pp. 1612-1618 (8 pages).
Kinjo, "Single molecule protein, nucleic acid, and enzyme assays and their procedures; Single molecule detection by fluorescence correlation spectroscopy", Proteins, Nucleic Acids and Enzymes, 1999, vol. 44, No. 9, pp. 1431-1438, w/English translation (22 pages).
Meyer-Almes, "Nanoparticle Immunoassays: A new Method for Use in Molecular Diagnostics and High Throughput Pharmaceutical Screening based on Fluorescence Correlation Spectroscopy", Fluorescence Correlation Spectroscopy Theory and Applications, Chemical Physics, 2000, pp. 204-224 (23 pages).
Katoh, Noriko et al., "A single molecule analyzer that enable new analysis of DNA and protein interaction", Genetic Medicine, 2002, vol. 6, No. 2, pp. 271-277(8 pages).
Goodwin et al. "Rapid sizing of individual fluorescently stained DNA fragments by flow cytometry," Nucleic Acids Research, 1993, vol. 21, No. 4, pp. 803-806 (4 pages).
Keller et al. "Single-Molecule Fluorescence Analysis in Solution," Applied Spectroscopy, 1996, vol. 50, No. 7, pp. 12A-32A (21 pages).
Lee et al. "Laser-Induced Fluorescence Detection of a Single Molecule in a Capillary," Analytical Chemistry, Dec. 1, 1994, vol. 66, No. 23, pp. 4142-4149 (8 pages).
Li et al. "Ultrasensitive Coincidence Fluorescence Detection of Single DNA Molecules", Analytical Chemistry, Apr. 1, 2003, vol. 75, No. 7, pp. 1664-1670 (7 pages).
Nie et al. "Probing Individual Molecules with Confocal Fluorescence Microscopy," Science, Nov. 11, 1994, vol. 266, pp. 1018-1021 (4 pages).
Tahari, "Fluorescence Correlation Spectroscopy: Ultrasensitive Detection in Clear and Turbid Media", University of Ilinois, 2005, pp. 1-88 (94 pages).
Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159 (3 pages).
Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830 (8 pages).
Carlsson et al, "Three-dimensional microscopy using a confocal laser scanning microscope", Optics Letiers, Optical Society of America, Feb. 1985, vol. 10, No. 2, pp. 53-55, XP007922413 (3 pages).
Kask et al."Two-Dimensional Fluorescence Intensity Distribution Analysis: Theory and Applications", Biophysical Journal, the Biophysical Society, Apr. 2000, vol. 78, pp. 1703-1713 (11 pages).
Kask et al."Fluorescence-intensity distribution analysis and its application in biomolecular detection technology", PNAS, Nov. 23, 1999, vol. 96 No. 24, pp. 13756-13761 (6 pages).
Bonnet et. al., "Kinetics of conformational fluctuations in DNA hairpin-loops", Proc. Natl. Acad. Sci. USA, Jul. 1998, vol. 95, pp. 8602-8606, cited in Specification of PCT/JP2015/084490 (6 pages).
International Search Report dated Aug. 14, 2012, issued in international application No. PCT/JP2012/067692, (counterpart of U.S. Appl. No. 14/178,442) (2 pages).
International Search Report dated Aug. 28, 2012, issued in international application No. PCT/JP2012/068947, (counterpart of U.S. Appl. No. 14/188,375) (2 pages).
International Search Report dated Feb. 14, 2012, issued in international application No. PCT/JP2012/051175, (counterpart of U.S. Appl. No. 13/946,091) (2 pages).
U.S. Final Office Action dated May 13, 2014, issued in related U.S. Appl. No. 13/946,091 (15 pages).
U.S. Non-Final Office Action dated Apr. 16, 2015. issued in related U.S. Appl. No. 13/946,091 (21 pages).
U.S. Final Office Action dated Sep. 29, 2015, issued in corresponding U.S. Appl. No. 13/946,091 (23 pages).
U.S. Advisory Action dated Feb. 2, 2016, issued in corresponding U.S. Appl. No. 13/946,091 (5 pages).
U.S. Non-Final Office Action dated Mar. 2, 2017, issued in U.S. Appl. No. 13/946,091 (13 pages).
U.S. Non-Final Office Action dated Jun. 24, 2016, issued in U.S. Appl. No. 14/188,375, (9 pages).
U.S. Final Office Action dated Dec. 29, 2016, issued in U.S. Appl. No. 14/188,375 (71 pages).
U.S. Final Office Action dated May 25, 2017, issued in U.S. Appl. No. 14/188,375 (9 pages).
U.S. Final Office Action dated Nov. 1, 2017, issued in U.S. Appl. No. 14/188,375 (9 pages).
U.S. Non-Final Office Action dated Feb. 6, 2014, issued in related U.S. Appl. No. 13/946,091 (11 pages).
U.S. Non-Final Office Action dated Nov. 16, 2015, issued in U.S. Appl. No. 14/178,442 (43 pages).

(56) References Cited

OTHER PUBLICATIONS

Chinese Office Action dated Oct. 10, 2014, issued in related Chinese application No. 201280005999.8; w/English Translation. (20 pages).
Chinese Office Action dated Jun. 1, 2015, issued in related Chinese application No. 201280005999.8, with English translation (15 pages).

* cited by examiner

FIG.1A
FIG.1B
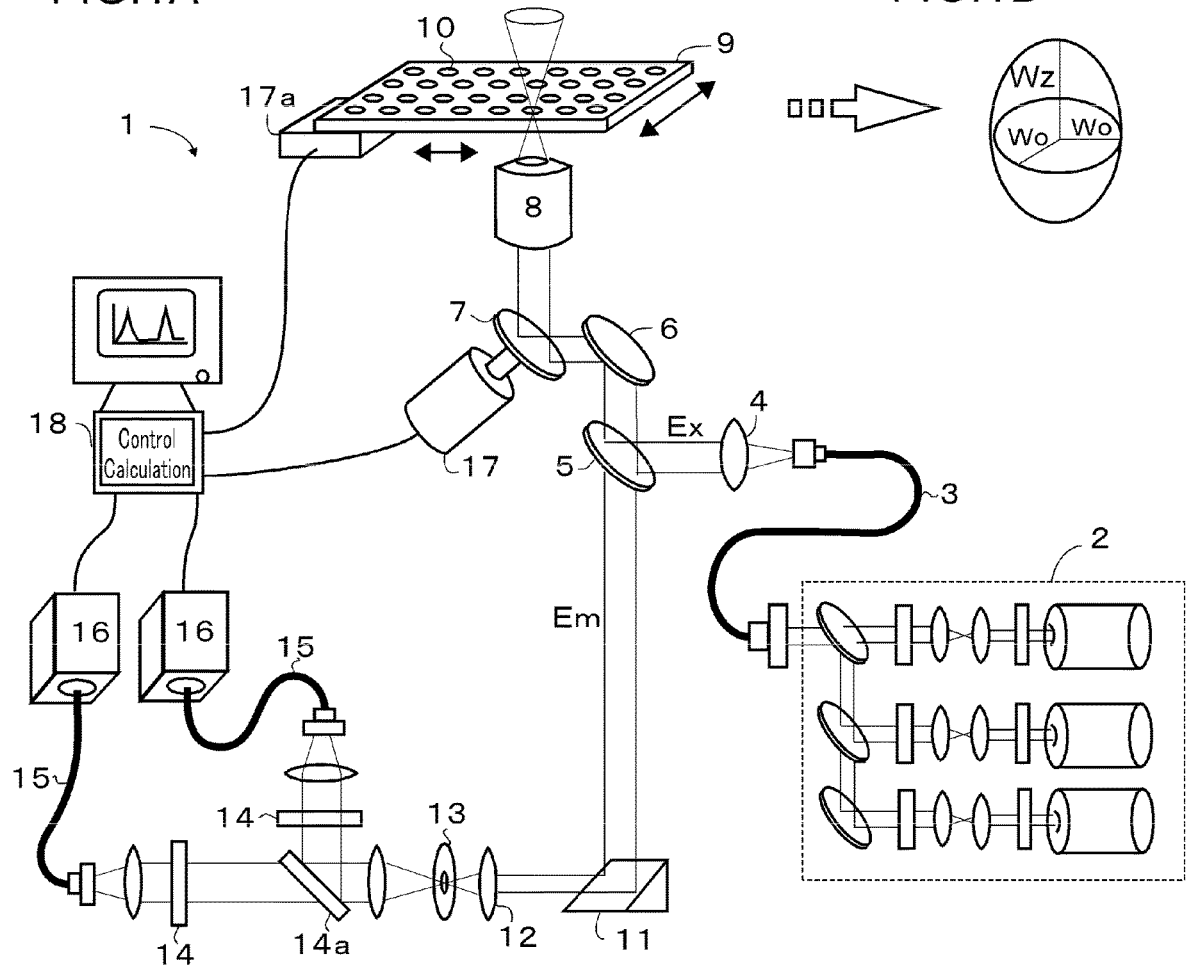
FIG.1C
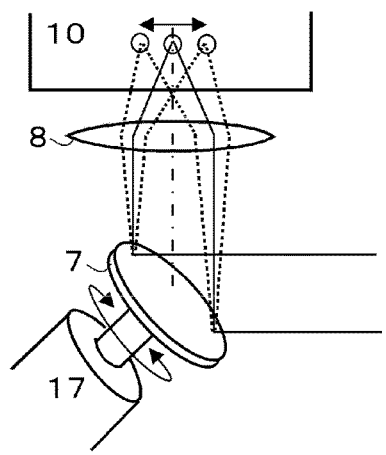
FIG.1D
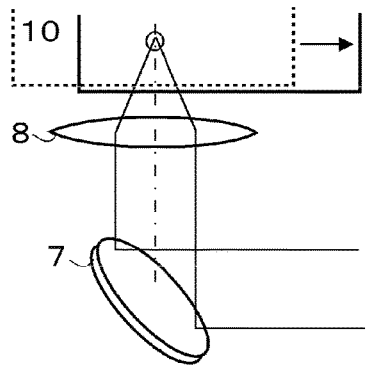

```
SEQUENCE LISTING

<160> NUMBER OF SEQ ID NOS: 2

<210> SEQ ID NO 1
<211> LENGTH: 28
<212> TYPE: DNA
<213> ORGANISM: Artificial
<220> FEATURE:
<223> OTHER INFORMATION: used for a test in a scanning molecule counting
      method

<400> SEQUENCE: 1
cctacgccaa cagctccaac tacgtagg                                             28

<210> SEQ ID NO 2
<211> LENGTH: 45
<212> TYPE: DNA
<213> ORGANISM: Artificial
<220> FEATURE:
<223> OTHER INFORMATION: used for a test in a scanning molecule method

<400> SEQUENCE: 2
tgactgaata taaacttgtg gtagttggag ctggtggcgt aggca                          45
```

OPTICAL ANALYSIS METHOD AND OPTICAL ANALYSIS DEVICE USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope, which can detect light from a micro region in a solution, to acquire useful information in an analysis of conditions (an interaction, a binding or dissociating condition, etc.) of particles, and more specifically, relates to an optical analysis device and an optical analysis method which detect individually the light from a single particle which emits light, using an optical system as described above, to make it possible to conduct various optical analyses. In this regard, in this specification, a particle which emits light (hereafter, referred to as a "light-emitting particle") may be any of a particle which emits light by itself and a particle to which an arbitrary light-emitting label or light-emitting probe has been attached, and the light emitted from a light-emitting particle may be fluorescence, phosphorescence, scattered light, chemiluminescence, bioluminescence, etc.

BACKGROUND ART

According to the developments in optical measurement techniques in recent years, detection and/or measurement of faint light at the single photon or single fluorescent molecule level have become possible by using an optical system of a confocal microscope and a super high sensitive light detection technique capable of the photon counting (single photon detection). Thus, there are variously proposed optical analysis techniques of performing detection of a characteristic, an intermolecular interaction, a binding or dissociating reaction of a biological molecule, etc. by means of such a faint light measurement technique. As such optical analysis techniques, for examples, there are known Fluorescence Correlation Spectroscopy (FCS, see e.g. patent documents 1-3 and non-patent documents 1-3), Fluorescence Intensity Distribution Analysis (FIDA, e.g. patent document 4, non-patent document 4) and Photon Counting Histogram (PCH, e.g. patent document 5). In addition, in patent documents 6-8, there are proposed methods of detecting fluorescent substances based on a time progress of a fluorescence signal of a sample solution measured using the optical system of a confocal microscope.

Furthermore, in patent documents 9-13, Applicant of the present application has proposed a novel optical analysis technique, using an optical system which is capable of detecting the light from a micro region in a solution, such as an optical system of a confocal microscope or a multiphoton microscope, and employing a different principle from optical analysis techniques, such as FCS and FIDA. In the case of the novel optical analysis technique (Hereinafter, referred to as "Scanning Molecule Counting Method".), the position of a micro area which is a detected region of light in a sample solution (Hereinafter, referred to as a "light detection region". When excitation light is used, it almost coincides with the condensing region of the excitation light.) is moved, i.e., the inside of the sample solution is scanned with the light detection region, and when the light detection region encompasses a light-emitting particle being dispersed and moving at random in the sample solution, the light emitted from the light-emitting particle is individually detected, and thereby each of the light-emitting particles in the sample solution is detected individually so that it becomes possible to perform the counting of the light-emitting particles and the acquisition of the information about the concentration or number density of the light-emitting particles in the sample solution.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent document 9: WO2011/108369
Patent document 10: WO2011/108370
Patent document 11: WO2011/108371
Patent document 12: WO2012/014778
Patent document 13: WO2013/024650

Non-Patent Documents

Non-patent document 1: G. Bonnet, et al., Proc. Natl. Acad. Sci. USA. Vol. 95, 8602-8606, (1998)

SUMMARY OF INVENTION

Technical Problem

In the detection of a light-emitting particle by the above-mentioned "Scanning Molecule Counting Method", when particles to be objects to be observed (particles to be observed) do not emit light, as one way of detecting such particles to be observed, a light-emitting probe is made bound with a particle to be observed and the light emitted from the light-emitting probe bound with the particle to be observed is detected, so that the existence of the particle to be observed can be detected (Patent documents 12 and 13). For such light-emitting probes, a light-emitting probe which does not substantially emit light in a state where the probe is not bound with a particle to be observed (hereinafter, referred to as an "unbound state") but emits light only in a state where the probe is bound with a particle to be observed (hereinafter, referred to as a "bound state") in the wavelength band of the detected light, is preferable (Hereafter, unless noted otherwise, when it is said that "a light-emitting probe emits light", it is meant that the probe emits light detectable with a photodetector in the wavelength band of detected light, while when it is said that "a light-emitting probe does not emit light", it is meant that the probe emits no light in the wavelength band of detected light, or that, even if the light is emitted in the wavelength band of detected light, its intensity is too low to be detected with a photodetector.). The reason for this is that such light-emitting probes do not emit light in the unbound state (hereafter, referred to as an "unbound probe"), so that, after mixing light-emitting probes into a sample solution containing particles to be observed or a sample solution to be tested with respect to whether particles to be observed are included or not, only light-emitting probes bound with a particle to be observed (hereafter, referred to as a "bound probe") will be detected with the light emitted by them even when unbound probes exist in the sample solution, and therefore, the process for removing unbound probes from the sample solution becomes unnecessary for an optical measurement. In such light-emitting probes, many of them come into a light-emitting state through an occurrence of change in a molecular structure caused with the binding to a particle to be observed, and for such examples, there are raised Molecular beacon, qBody, an intercalator molecule of which fluorescence changes by binding to nucleic acid, a molecule obtained by binding with nucleic acid an intercalator molecule of which fluorescence changes by binding to nucleic acid, a molecule obtained by binding a fluorescent molecule and a quenching molecule to an aptamer, etc. Further, for intercalator molecules, there are raised Hoechst 33258, Hoechst 33342, DAPI, 9-amino-6-chloro-2-methoxyacridine(ACMA), acridine homodimer(bis-(6-chloro-2-methoxy-9-acridinyl)spermine), BOBO-1 iodide, SYTOX Green, YOYO-1, acridine orange, TOTO-1, Ethidium Bromide, BOBO-3 iodide, SYTOX Red, SYBR Green I, SYBR Green II, SYBR Glod, Pico Green, OliGreen, Gel Red, Gel Green, Ribo Green, EvaGreen, thiazol orange, etc.

However, in light-emitting probes which do not substantially emit light in an unbound state but emits light in a bound state as described above, generally, many of them temporarily get into a state where they emit light or a state where they are capable of emitting light (light-emitting state) even in an unbound state. Namely, in the cases of some light-emitting probes, even in an unbound probe, there can occur a stochastic transition between a non-light-emitting state that no light is emitted (a state that the probe does not emit light even when irradiated with excitation light) and a light-emitting state that light is emitted, and an unbound light-emitting probe will also emit light once a transition from the non-light-emitting state to the light-emitting state occurs until a transition from the light emitting state to the non-light-emitting state (A bound probe usually stably remains in the light-emitting state and rarely comes into the non-light-emitting state.). Thus, when light-emitting probes as described above are used in the Scanning Molecule Counting Method, in the light measurement performed while moving a light detection region within a sample solution (while scanning the inside of the sample solution), if an unbound probe passes through the inside of the light detection region, namely, if the light detection region passes through a region occupied by the unbound probe while being temporarily in the light-emitting state, the light from the unbound probe will be detected, and thereby, the unbound probe could be erroneously detected as a light-emitting particle (a bound probe). It is desirable that such an erroneous detection of an unbound probe can be avoided as much as possible since it causes the reduction of the precision or accuracy in detecting particles to be observed or light-emitting particles.

In this respect, the average length of the time in which an unbound probe is in a light-emitting state, namely, the average length of the time from a transition from the non-light-emitting state to the light-emitting state to a transition from the light-emitting state to the non-light-emitting state is determined depending upon the species of light-emitting probe and can be measured as an average lifetime (In this regard, "average lifetime" referred to here is the time length in which a molecule has a molecular structure of the light-emitting state, and is not meant to be a fluorescence lifetime.). Thus, in a case of using a certain kind of light-emitting probe in the above-mentioned scanning molecule counting method, if the average lifetime of the light-emitting state in an unbound probe is known, and thus, the moving speed of a light detection region is so adjusted that the length of the time for the unbound probe to pass through the inside of the light detection region will be longer than the average lifetime of its light-emitting state, it will be almost ensured that there exists a section where the unbound probe is in the non-light-emitting state in a period during which the unbound probe passes through the inside of the light detection region, i.e., a period in which the unbound probe exists in the inside of the light detection region even when the unbound probe temporarily get into the light-emitting state. In that case, the total amount of the light detected in a period in which an unbound probe exists in the inside of the light detection region is reduced in comparison with a case that a light-emitting probe passes through the inside of the light detection region while staying in the light-emitting state, and further, the time in which light is detected also becomes much shorter, and thus, in the results of light measurements, a case that a light-emitting particle passes through the inside of the light detection region and a case that an unbound probe passes through the inside of the light detection region can be mutually distinguished. This knowledge is used in the present embodiment.

Thus, a main object of the present embodiment is to provide a structure improved so as to avoid erroneous detection of an unbound light-emitting probe as a light-emitting particle as much as possible in a case of detecting a particle formed by binding a light-emitting probe to a particle to be observed as a light-emitting particle in Scanning Molecule Counting method, wherein the light-emitting probe is a probe which emits light in a state that the probe is bound with a particle to be observed in the wavelength band of detected light, but substantially emits no light in a state that the probe is unbound from a particle to be observed in the wavelength band of the detected light, and in which probe, even in an unbound state that the probe is unbound from a particle to be observed, there occurs a stochastic transition between a non-light-emitting state that no light is emitted in the wavelength band of the detected light and a light-emitting state that light is emitted in the wavelength band of the detected light.

Solution to Problems

According to the present embodiment, the above-mentioned object is achieved by an optical analysis method of detecting light from light-emitting particles dispersed and moving at random in a sample solution using an optical system of a confocal microscope or a multiphoton microscope, comprising steps of: moving a position of a light detection region of the optical system of the microscope in the sample solution; measuring a light intensity from the light detection region during the moving of the position of the light detection region in the sample solution to generate time series light intensity data; and detecting individually each of signals of the light-emitting particles on the time series light intensity data; wherein the light-emitting particles are particles formed by binding to a particle to be observed a light-emitting probe which emits light in a wavelength band of the detected light by being bound to the particle to be observed and in which probe there occurs a stochastic transition between a non-light-emitting state that no light is emitted in the wavelength band of the detected light and a light-emitting state that light is emitted in the wavelength band of the detected light in a state that the probe is unbound from the particle to be observed; and wherein the step of moving the position of the light detection region comprises a step of adjusting a moving speed of the position of the light detection region to make an encompassing time during which the light-emitting probe unbound from the particle to be observed is encompassed by the moving light detection region longer than an average lifetime during which the light-emitting probe unbound from the particle to be observed is in the light-emitting state. In this regard, there is further conducted a step of counting the number of the signals of the light-emitting particles detected individually to determine a concentration of the light-emitting particles in the sample solution based on the number.

In this structure, "light-emitting particles dispersed and moving at random in a sample solution" may be particles, such as atoms, molecules or aggregates of these, which are dispersed or dissolved in a sample solution and emit light, and those may be arbitrary particulate matters making the Brownian motion freely in the solution without being fixed on a substrate, etc. The light-emitting particles are typically fluorescent particles, but may be particles which emit light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For light-emitting particles which emit light without illumination light, for example, molecule which emit light according to chemiluminescence or bioluminescence, no illumination light is required in the microscope.). Further, typically, in the above-mentioned light detection, the light from the light detection region is detected by the photon counting in which (a) photon(s) arriving in every predetermined measuring unit time (bin time) is/are counted, and in that case, the time series light intensity data becomes time series photon count data. The "light-emitting state" is a state that light is emitted by irradiation of excitation light (or addition of a specific substance (in the case of chemoluminescence and bioluminescence)), namely, a state that a probe has a light-emitting ability, while the "non-light-emitting state" is a state that a probe has no light-emitting ability as mentioned above. The "average lifetime during which the light-emitting probe . . . is in the light-emitting state" is an average lifetime of a molecular structure in which a probe is in the light-emitting state. In this connection, in this specification, "a signal of a light-emitting particle" means a signal expressing light from a light-emitting particle, unless noted otherwise.

As understood from the above, in the basic structure of the above-mentioned present embodiment, i.e., the scanning molecule counting method, the light detection is sequentially performed while the position of the light detection region is moved in a sample solution, namely, while the inside of the sample solution is scanned with the light detection region. Then, when the light detection region moving in the sample solution encompasses a randomly moving light-emitting particle, the light from the light-emitting particle is detected by the light detecting portion and thereby the existence of one particle will be detected. Thus, in the sequentially detected, time series light intensity data, a signal from a light-emitting particle is individually detected, and thereby, the existences of individual particles are detected one by one successively, and accordingly, diverse information on the conditions of the particles in the solution will be acquired. For concrete data processing, the processes described in patent documents 9-13 or other patent applications concerning the scanning molecule counting method by the applicant of the present application may be arbitrarily used. Concretely, for example, in the step of detecting each of signals of the light-emitting particles individually, the signal from each of the light-emitting particles may be detected individually by detecting individually, as a signal of one light-emitting particle, a time variation of the light intensity in the time series light intensity data which has a profile assumed in the light from one light-emitting particle which moves relatively the inside of the light detection region, and further, prior to the search of time variations of light intensity having a profile corresponding to a signal of a light-emitting particle in the time series light intensity data, the smoothing process of the time series light intensity data may be performed to the degree that lacks in data value vanish in the profile of the light intensity from a light-emitting particle, and the search of a signal of a light-emitting particle may be performed in the smoothed time series light intensity data.

In the above-mentioned structure, the inventive method is advantageously applied particularly in the case that a particle to be an object to be observed, i.e. a particle for which the presence or absence and/or the concentration in a sample solution or other characteristics are tested, is, for example, a particle which does not significantly emit light in the wavelength band of detected light, and thus, a "light-emitting particle" is formed by binding to the particle to be observed a light-emitting probe which emits light in the state that it is bound to the particle to be observed and the light of the so formed "light-emitting particle" is detected. In the light-emitting probes which emit light in the state that they are bound to particles to be observed, as already noted, depending upon kinds of the probes, a stochastic transition between a light-emitting state and a non-light-emitting state occurs in the probe even when a probe is in a state that it is unbound from a particle to be observed, and when the probe gets into the light-emitting state, it has a light-emitting ability during a period of certain degree, and then, if an unbound probe which gets temporarily into the light-emitting state passes relatively through the inside of the light detection region while the probe is in the light-emitting state, the unbound probe would be erroneously detected as a conjugate of a particle to be observed and a light-emitting probe, i.e. a light-emitting particle.

However, with respect to the length of the period during which an unbound probe is in a light-emitting state, there is determined an average length, i.e., an average lifetime, for each molecular species, and thus, if the period during which an unbound probe passes through the inside of the light detection region is longer than the average lifetime of the light-emitting state of the unbound probe, the total amount of the light intensity and the generation period of significant light intensity, measured in the period during which the unbound probe passes through the inside of the light detection region, reduces as compared with the case of a bound probe which continues emitting light substantially while passing through the inside of the light detection region, and in that case, the time variation of the light intensity from an unbound probe can be distinguished from that of a light-emitting particle. In this respect, the length of the period during which a bound probe (light-emitting particle) or an unbound probe passes through the inside of a light detection region, i.e., the length of the time in which a bound probe or an unbound probe is encompassed in the inside of the light detection region, is determined by the moving speed of the position of the light detection region. Thus, in the present embodiment, in order to make it possible to distinguish the time variation of the light intensity in a case that an unbound probe being temporarily in the light-emitting state is encompassed by a light detection region from the time variation of the light intensity in a case that a bound probe, i.e., a light-emitting particle, passes through a light detection region relatively while being in the light-emitting state, as noted above, there is performed the step of adjusting a moving speed of the position of the light detection region to make an encompassing time during which the light-emitting probe unbound from the particle to be observed is encompassed by the moving light detection region longer than an average lifetime during which the light-emitting probe unbound from the particle to be observed is in the light-emitting state. In this regard, the "average lifetime" in which a light-emitting probe is an unbound probe and in the light-emitting state can be measured by a preparatory experiment beforehand or can be determined with reference to an arbitrary literature value. Accordingly, in the adjustment of the moving speed of the position of the light detection region, a concrete moving speed may be set with reference to the preliminarily investigated value of the average lifetime in which an unbound probe is in the light-emitting state with respect to the light-emitting probe to be used. And, as noted, since the above-mentioned "average lifetime" is usually determined according to the molecular species of light-emitting probe, the moving speed of the position of the light detection region may be determined based on the molecular species information of the light-emitting probe.

In the above-mentioned structure, since the light-emitting particles and light-emitting probes are considered, with respect to their sizes, as infinitesimal points relative to a light detection region, the encompassing time during which a light-emitting probe unbound from a particle to be observed is encompassed by the moving light detection region is the time until the light detection region moves the distance equal to its size in its moving direction. Thus, concretely, in order to make the time taken for the light detection region to move its size in its moving direction longer than the "average lifetime" in which an unbound probe is in the light-emitting state, the moving speed u of the position of the light detection region may be set lower than the value obtained by dividing the size d of the light detection region in its moving direction by the average lifetime τ of the light-emitting probe. Further, more preferably, the moving speed u of the position of the light detection region may be set to satisfy a conditional expression:

$$u < d/(e\tau) \quad (1),$$

where e is the base of natural logarithm. It has been found as explained later that, when the moving speed u of the position of the light detection region satisfies the expression (1), even under assumption that an unbound probe emits light for the average lifetime τ while being encompassed by the moving light detection region, the total amount of the light from the unbound probe becomes small enough effectually to an ignorable level.

Moreover, in the above-mentioned inventive method, the light-emitting probe may be a molecule from which emitted light intensity changes with an intramolecular structural change known as, for example, molecular beacon, qbody, intercalator to be bound with nucleic acid, aptamer formed by binding a fluorescent molecule to a quenching molecule. Also, the light-emitting probe may be a probe formed by a fluorescent intercalator molecule binding to nucleic acid. Or, the light-emitting probe may be formed by a first probe to be an energy donor in a fluorescence energy transfer phenomenon and a second probe to be an energy acceptor in the fluorescence energy transfer phenomenon, wherein light is emitted by the second probe through the fluorescence energy transfer phenomenon occurring when both the first and second probes are bound to a particle to be observed (Accordingly, the first probe and second probe are molecules mutually separated in a state that they are unbound from the particle to be observed.). In this case, the detected light from the probe bound to the particle to be observed is the light emitted by the second probe. Moreover, the first probe, the second probe or both the first and second probes may be a molecule from which emitted light intensity changes in accordance with an intramolecular structural change. Furthermore, by binding a light-emitting probe with a molecule to be an energy acceptor in a light-emitting energy transfer phenomenon, the emission wavelength may be changed to be easier for observation.

The above-mentioned inventive method is realized by an optical analysis device as described in patent documents 9-13, etc., wherein especially the moving speed of the position of the light detection region is set such that the encompassing time during which a light-emitting probe unbound from a particle to be observed is encompassed by the moving light detection region will be longer than an average lifetime during which the light-emitting probe unbound from the particle to be observed is in the light-emitting state. Thus, in another aspect of the present embodiment, there is provided an optical analysis device which detects light from light-emitting particles dispersed and moving at random in a sample solution using an optical system of a confocal microscope or a multiphoton microscope, comprising: a light detection region moving portion which relatively moves a position of a light detection region of the optical system of the microscope in the sample solution; a light detecting portion which detects light from the light detection region; and a signal processing portion which generates time series light intensity data of the light from the light detection region detected with the light detecting portion during the moving of the position of the light detection region in the sample solution and detects each of signals of the light-emitting particles individually in the time series light intensity data; wherein the light-emitting particles are particles formed by binding a particle to be observed with a light-emitting probe which emits light in a wavelength band of the detected light by being bound to the particle to be observed and in which probe there occurs a stochastic transition between a non-light-emitting state that no light is substantially emitted in the wavelength band of the detected light and a light-emitting state that light is substantially emitted in the wavelength band of the detected light in a state that the probe is unbound from a particle to be observed; and wherein a moving speed of the position of the light detection region moved by the light detection region moving portion is set to make an encompassing time during which the light-emitting probe unbound from the particle to be observed is encompassed by the moving light detection region longer than an average lifetime during which the light-emitting probe unbound from the particle to be observed is in the light-emitting state.

In the case of the above-mentioned inventive device, the moving speed of the position of the light detection region may be determined based on the molecular species information of the light-emitting probe, and concretely may be set smaller than the value obtained by dividing the size d of the light detection region in its moving direction by the average lifetime τ of the light-emitting probe. And, more preferably, the moving speed u of the position of the light detection region may be set to satisfy a conditional expression expressed with the base of natural logarithm e:

$$u<d/(e\tau) \quad (1).$$

For example, the data of average lifetime values of light-emitting states when probes are in unbound states for plural molecular species of light-emitting probes may be memorized beforehand in a memory, so that, when a user inputs molecular species information of a light-emitting probe to be used for a measurement, the value of the average lifetime corresponding to the input will be read out and used for the determination of the moving speed of the position of the light detection region.

The optical analysis technique of the above-mentioned present embodiment is used, typically, for an analysis of a condition in a solution of a biological particulate object, such as a biological molecule, e.g. a protein, a peptide, a nucleic acid, a lipid, a sugar chain, an amino acid or these aggregate, a virus, an exosome and a cell, etc., but it may be used for an analysis of a condition in a solution of a non-biological particle (for example, an atom, a molecule, a micelle, a metallic colloid, etc.), and it should be understood that such a case belongs to the scope of the present invention also. The way and manner of moving the position of a light detection region relative to a sample solution, the way and manner of extracting or detecting the signal of each light-emitting particle from the light intensity value in time series light intensity data, the way and manner of determining parameters for determining an absolute concentration value, etc. may be similar to ways and manners described in patent documents 9-13, etc.

Effect of Invention

Thus, according to the above-mentioned inventive structure, in a case that a light-emitting particle is a particle formed by binding a particle to be observed with a light-emitting probe which emits light in a wavelength band of the detected light by being bound to the particle to be observed and in which probe there occurs a stochastic transition between a non-light-emitting state that no light is substantially emitted in the wavelength band of the detected light and a light-emitting state that light is substantially emitted in the wavelength band of the detected light in a state that the probe is unbound from a particle to be observed, even when a moving light detection region encompasses a light-emitting probe unbound from a particle to be observed and the light-emitting probe has been in or gets into the light-emitting state, since the time taken for the light-emitting probe to pass through the inside of the light detection region is longer than the average lifetime of the light-emitting state, there almost surely exists a time in which the light-emitting probe is in the non-light-emitting state. Then, the time variation of the light intensity over the time during which the light-emitting probe passes through the inside of the light detection region can be distinguished from the case of a bound probe (a light-emitting particle) which passes through the inside of the light detection region while being bound to a particle to be observed and emitting light, and therefore, it is expected that the possibility of erroneously detecting an unbound probe as a light-emitting particle is greatly reduced, and it becomes possible to detect selectively the signals of bound probes, i.e., light-emitting particles. And, according to this structure, the necessity for the process of removing unbound probes from a sample solution will further be reduced, and thus, there can be obtained an advantage that it also becomes unnecessary to take into consideration the loss of the sample which has been caused in a case that the process of removing unbound probes is performed. This will be advantageous especially in analyses using rare or expensive samples Other purposes and advantages of the present embodiments will become clear by explanations of the following preferable embodiments.

BRIEF DESCRIPTIONS OF DRAWINGS

FIG. 1A is a schematic diagram of the internal structure of an optical analysis device with which the scanning molecule counting method is performed according to the present embodiment. FIG. 1B is a schematic diagram of a confocal volume (an observation region of a confocal microscope). FIG. 1C is a schematic diagram of the mechanism for changing the direction of a mirror 7 to move the position of a light detection region in a sample solution. FIG. 1D is a schematic diagram of the mechanism which moves the horizontal position of a micro plate to move the position of a light detection region in a sample solution.

Figure 2B:
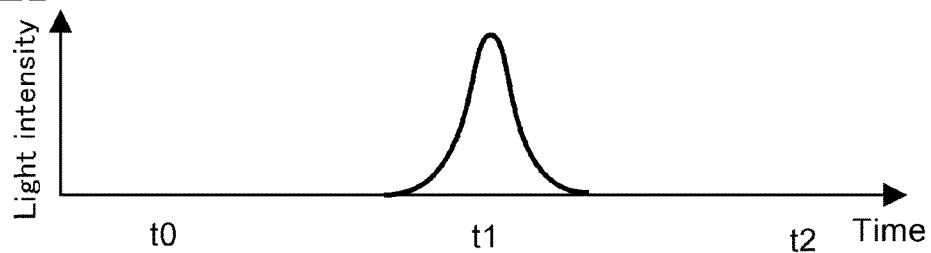

FIGS. 2A and 2B are a schematic diagram explaining the principle of the light detection and a schematic diagram of the variation of the measured light intensity with time in the scanning molecule counting method to which the present embodiment is applied, respectively.

Figure 3A:
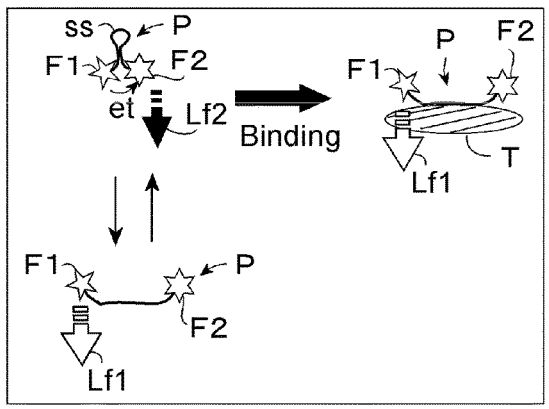
Figure 3B:
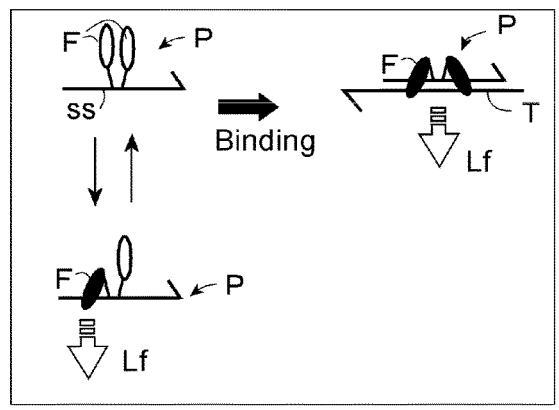
Figure 3C:
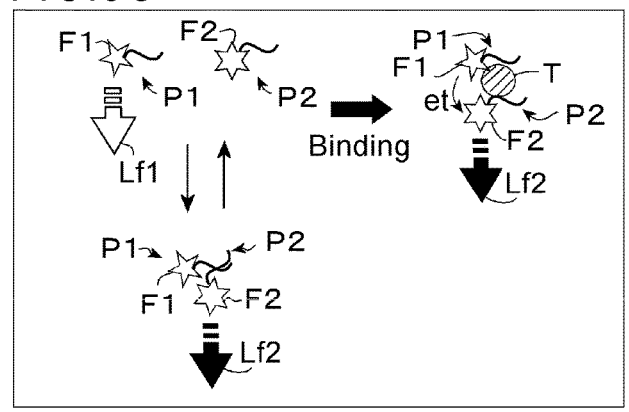

FIGS. 3A-3C are model drawings of reactions of light-emitting probes P which emit light when they bind with particles to be observed T. FIG. 3A shows a case that the light-emitting probe P is a molecular beacon; FIG. 3B shows a case that the light-emitting probe P is a single strand nucleic acid molecule to which a fluorescent intercalator molecule has been added; and FIG. 3C shows a case that the light-emitting probe consists of two probes: a first probe P1 and a second probe P2.

Figure 4A:
Figure 4A:
Figure 4A:
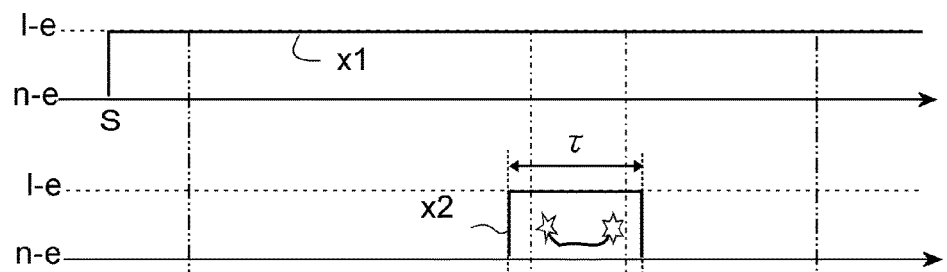
Figure 4B:
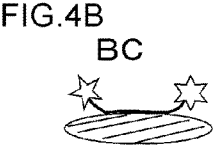
Figure 4B:
Figure 4B:
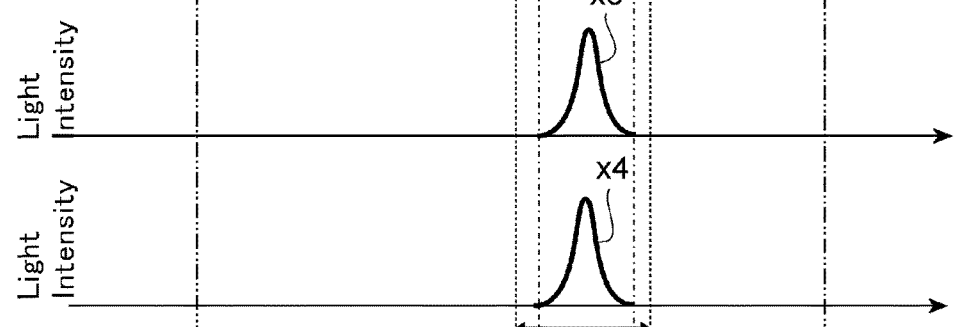
Figure 4C:
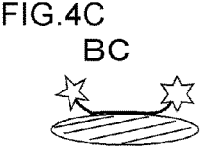
Figure 4C:
Figure 4C:
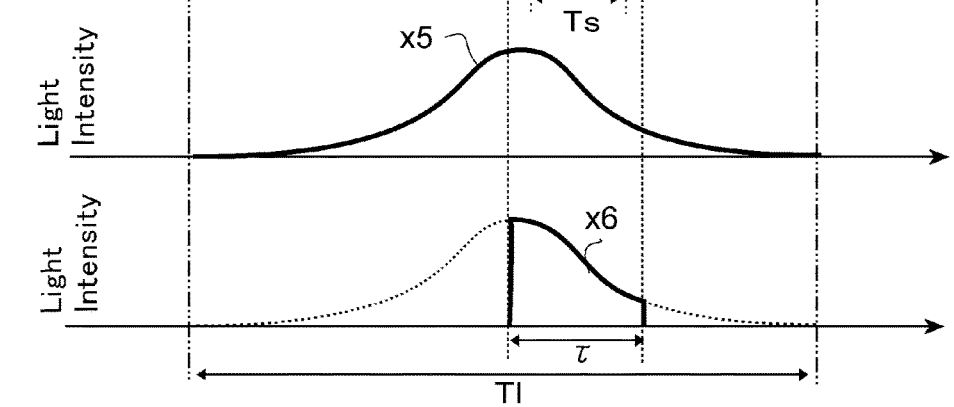

FIG. 4A shows periods of the light-emitting state of a light-emitting probe being in a state BC that it is bound to a particle to be observed and in a state N-BC that it is unbound from a particle to be observed, respectively; and FIGS. 4B and 4C show time variations of the light intensity detected when each light-emitting probe is encompassed by a light detection region.

FIG. 4B shows a case that the time Ts during which a light-emitting probe is encompassed by the light detection region is shorter than the average lifetime τ of the light-emitting state of the unbound probe; and FIG. 4C shows a case that the time Tl during which a light-emitting probe is encompassed by the light detection region is longer than the average lifetime τ of the light-emitting state of the unbound probe.

Figure 5:
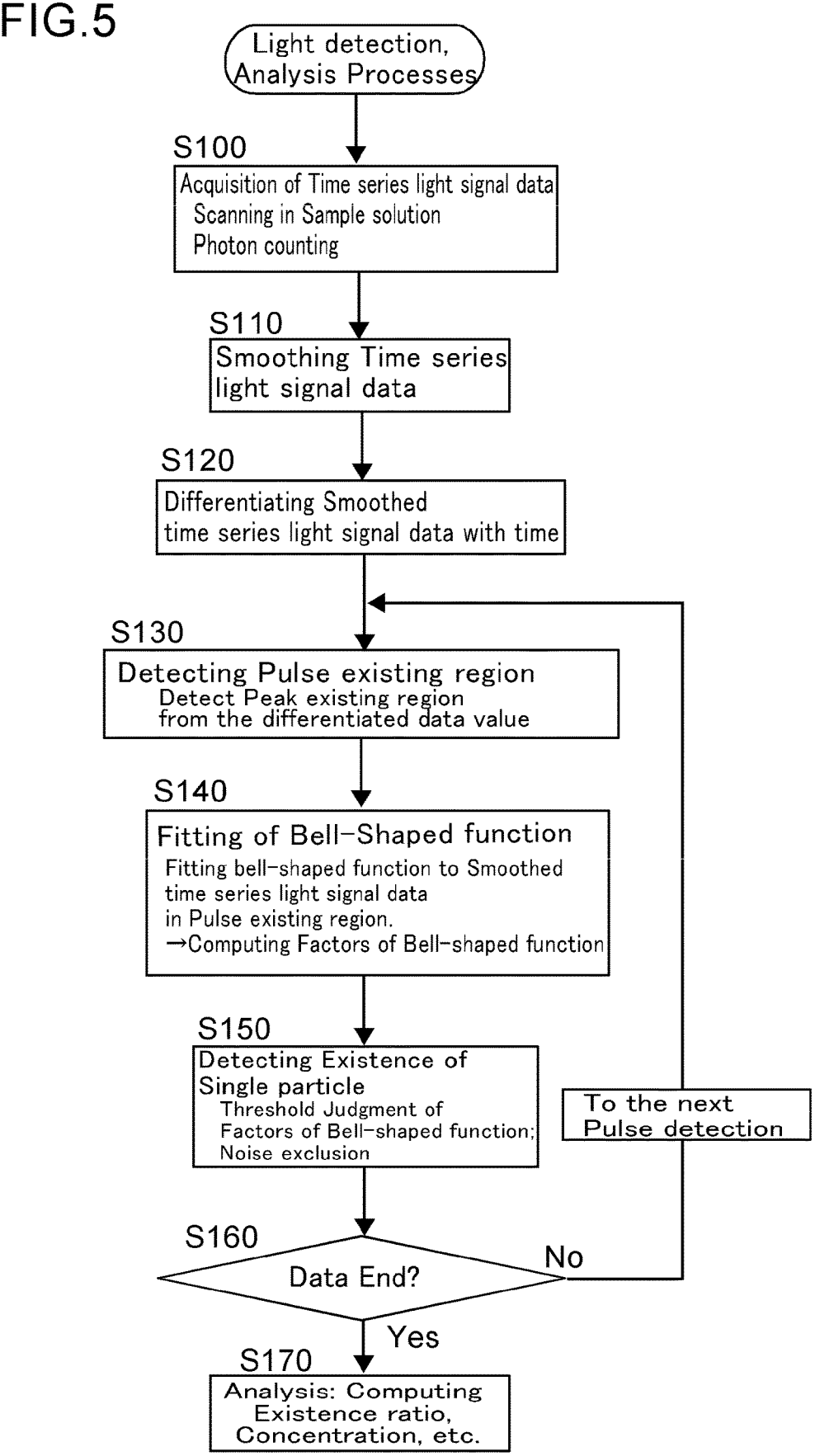

FIG. 5 is a drawing which shows procedures of the scanning molecule counting method to which the present embodiment is applied in the form of flow chart.

Figure 6A:
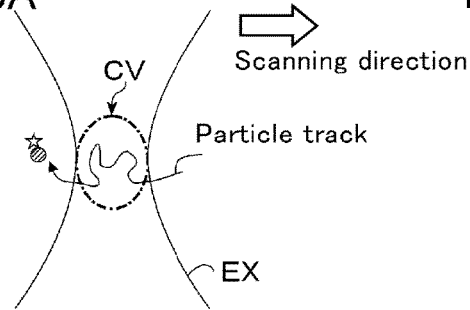
Figure 6B:
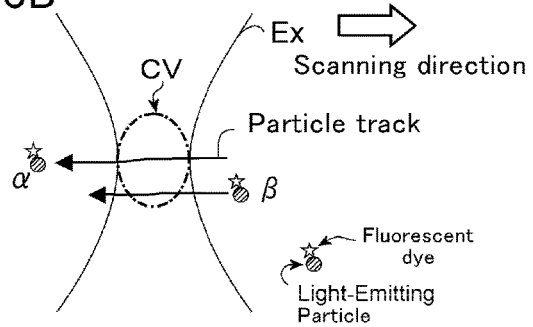
Figure 6C:
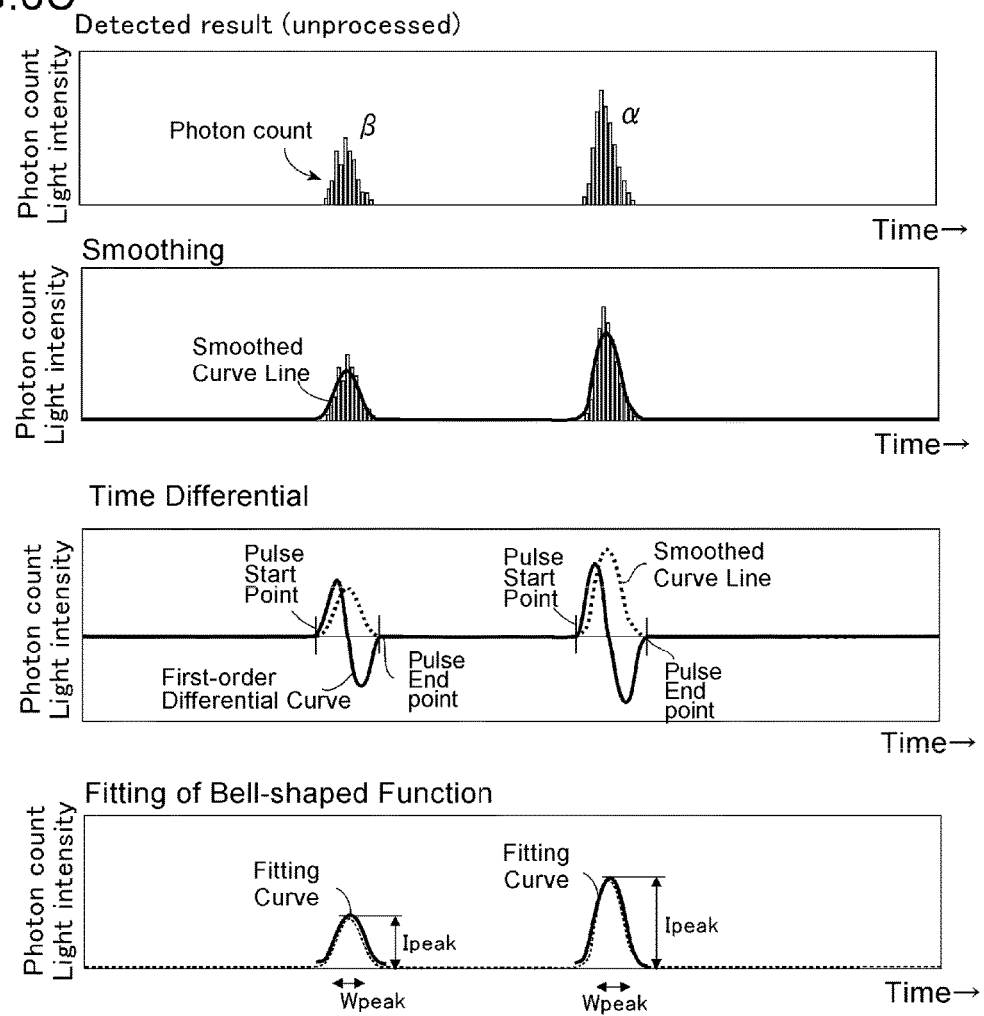
Figure 6D:
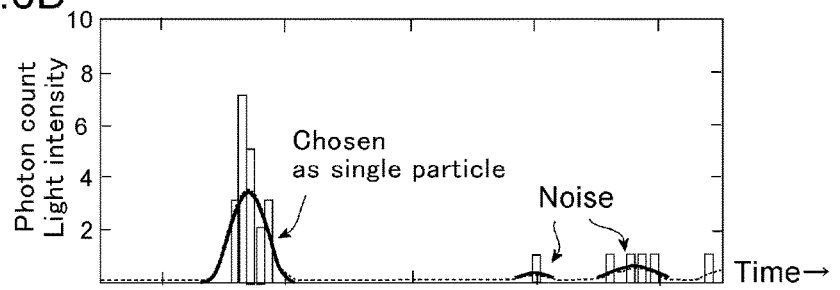

FIGS. 6A and 6B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 6C shows drawings explaining an example of the signal processing step of the detected signals in the procedure for detecting the existence of a light-emitting particle from the measured time series light intensity data (change in time of photon count) in accordance with the scanning molecule counting method. FIG. 6D shows examples of measured photon count data (bar graph); curves obtained by carrying out the smoothing of the data (dotted line); and Gauss functions fitted on the pulse existing region (solid line). In the drawing, the signals labeled "noise" are disregarded as signals due to noises or contaminants.

Figure 7A:
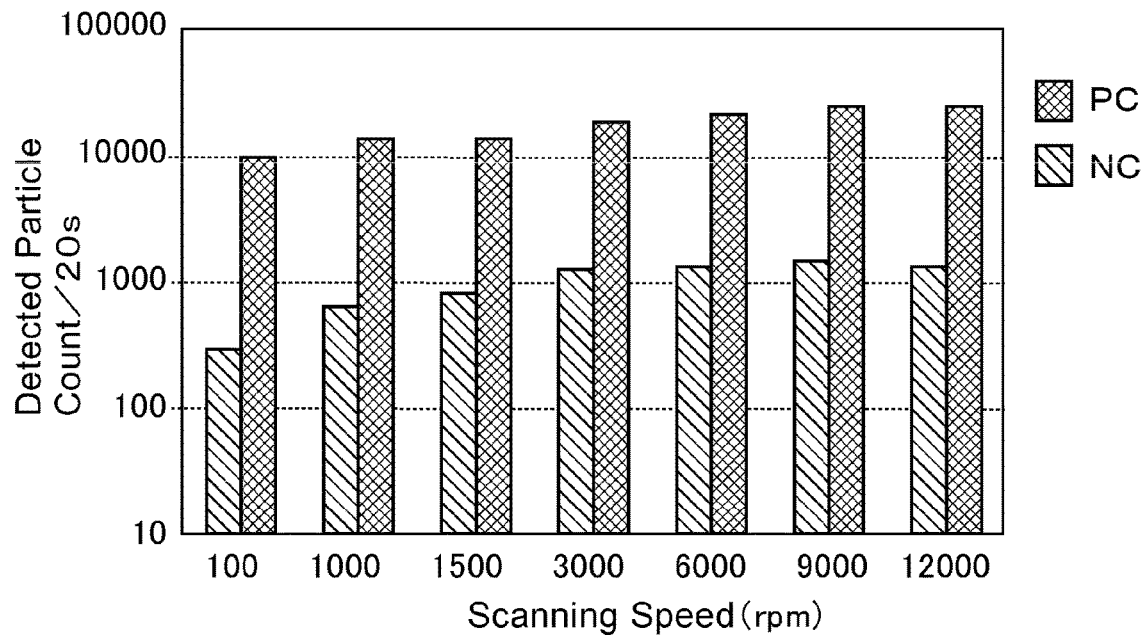
Figure 7B:
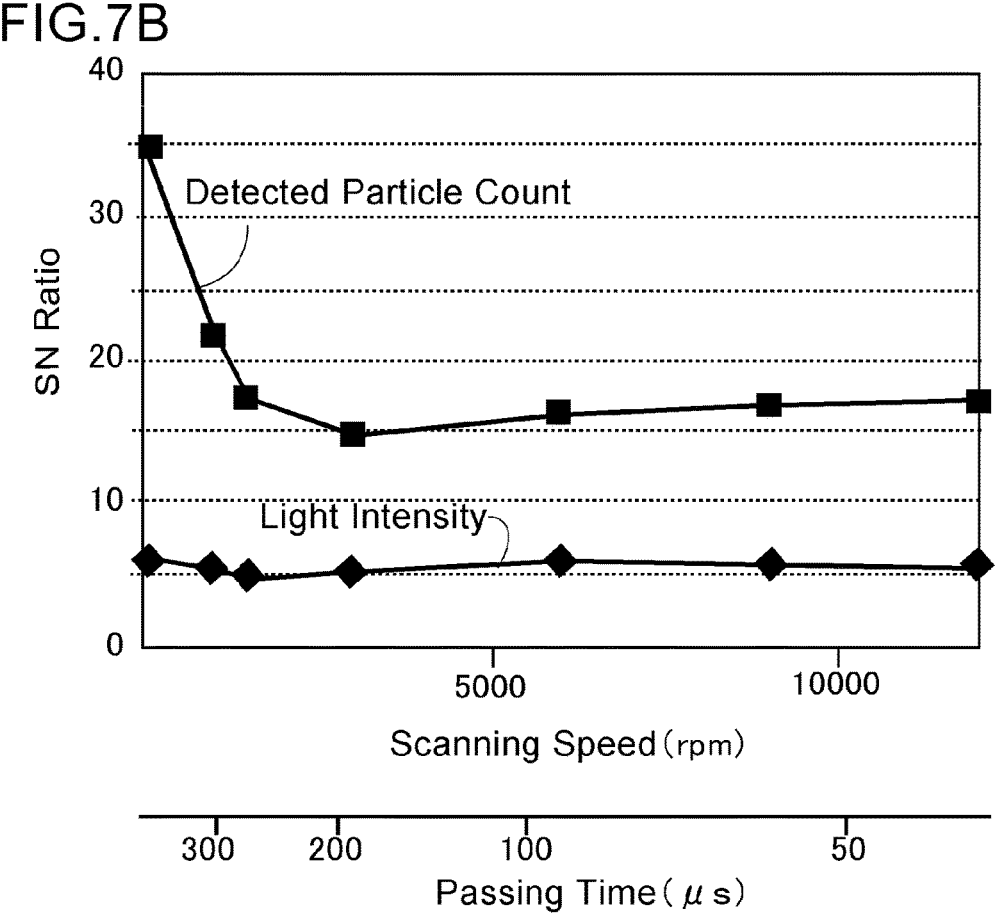

FIG. 7A shows particle counts of light-emitting particles (single light-emitting probes or conjugates of light-emitting probe and particle to be observed) detected by the scanning molecule counting method in which light measurements were performed at various scanning speeds (moving speeds of the position) of the light detection region in Embodiment 1. In the drawing, values are the detected counts of particles per 20 seconds in the case of performing light measurements with scanning by the light detection region. NC shows the case that only single light-emitting probes were contained in a sample solution, while PC shows the case that conjugates of light-emitting probe and particle to be observed were contained in a sample solution (in this case, single light-emitting probes (unbound probes) were rarely contained.). FIG. 7B shows signal to noise ratios of the detected counts of light-emitting particles detected by the scanning molecule counting method in which light measurements were performed at various scanning speeds (moving speeds of the position) of the light detection region in Embodiment 1. In this regard, here, the signal to noise ratio was computed as a ratio of the value of PC to the value of NC in FIG. 7A. For comparison, signal to noise ratios of the measured light intensities (ratios of light intensity value in the case of NC to in the case of PC) are also shown.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a - - - Dichroic mirror or Polarization beam splitter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments are described in detail.

Structure of Optical Analysis Device

In the basic structure, an optical analysis device which realizes the optical analysis technique according to the present embodiment is a device constructed by associating the optical system of a confocal microscope and a photodetector, enabling the scanning molecule counting method as described in patent documents 9-13, as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA (numerical aperture) at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later.

In the above-mentioned structure, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with an approximately bell-shaped distribution (a Gaussian type distribution) having the peak at the center of the region. The effective volume is a volume of an approximate ellipsoid bordering a surface where the light intensity is reduced to $1/e^2$ of the center light intensity.), which focal region is called as "confocal volume".

Furthermore, in the present embodiment, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 17*a* for moving the horizontal position of the micro plate 9, in order to change the well 10 to be observed. The operation of the stage position changing apparatus 17*a* may be controlled by the computer 18. According to this structure, quick measurements can be achieved even when there are two or more specimens.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of moving the absolute position of a light detection region). This mirror deflector 17 may be the same as that of a galvanomirror device equipped on a usual laser scan type microscope. Or, alternatively, as illustrated in FIG. 1D, the stage position changing apparatus 17*a* may be operated in order to move the horizontal position of the container 10 (micro plate 9), into which the sample solution has been dispensed, to move the relative position of the light detection region in the sample solution (the type of moving the absolute position of a sample solution). Moreover, together with making the light detection region circulate along a scanning track in the way of moving the absolute position of a light detection region by changing the optical path, the position of the scanning track of the light detection region in the sample solution may be moved along a predetermined moving route in the way of moving the position of the sample solution. In either of the ways, in order to attain a desired moving pattern of the position of the light detection region, the mirror deflector 17 and/or the stage position changing apparatus 17*a* are/is driven in harmony with the light detection of the photodetector 16 under the control of the computer 18. The scanning track of the position of the light detection region may be a closed cyclic route, such as a circle, an ellipse, etc., and the moving route of the position of the sample solution may be arbitrarily selected from circular, elliptical, straight and curvilinear ones and a combination of these (The program in the computer 18 may be designed so that various moving patterns can be selected.) In this regard, although not illustrated, the position of the light detection region may be moved in the vertical direction by moving the objective 8 or stage up and down.

In a case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in a case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may be provided, and thereby, it may be designed that, when two or more kinds of light-emitting particle having different emission wavelengths are included in the sample, the light therefrom can be detected separately in accordance with the wavelengths. Furthermore, in the optical analysis device 1, two or more excitation light sources 2 may be provided as shown in the drawing, and the wavelength of excitation light can be appropriately selected, depending upon the excitation wave length of light-emitting particles. Similarly, two or more photodetectors 16 may be installed so that, in a case that two or more kinds of light-emitting particles having different wavelengths are contained in the sample, the lights from those can be separately detected in accordance with their wavelengths The computer 18 has a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

By the way, as explained in detail later, the present embodiment can be applied advantageously to a case that the above-mentioned light-emitting particle is a conjugate of a particle to be an object to be observed (particle to be observed) and a light-emitting probe, especially wherein the light-emitting probe, when bound with a particle to be observed, is stably in a light-emitting state while the light-emitting probe, when unbound from a particle to be observed, is basically in a non-light-emitting state but temporarily gets into the light-emitting state. Further, as explained in detail later, in the inventive scanning molecule counting method, for the moving speed of the position of the above-mentioned light detection region, i.e., the scanning speed at which the light detection region is scanning the inside of a sample solution, the preferable lower limit is set according to the diffusion moving velocity of the detected light-emitting particle while the more preferable upper limit is set based upon the average lifetime of the light-emitting state of a light-emitting probe unbound from a particle to be detected (unbound probe) contained in the sample solution.

Principle of Scanning Molecule Counting Method and Setting of Scanning Speed

1. Principle of Scanning Molecule Counting Method

In the scanning molecule counting method (patent documents 9-13), the light detection is performed together with moving the position of a light detection region CV in a sample solution, namely, scanning the inside of the sample solution with the light detection region CV by driving the mechanism for moving the position of the light detection region to change the optical path (mirror deflector 17) or by moving the horizontal position of the container 10 (micro plate 9) into which the sample solution is dispensed, as schematically drawn in FIG. 2A.

Then, for example, during the moving of the light detection region CV (in the drawing, time t0-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (a time variation of significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Improvement in the Present Embodiment

As already noted, the particle to be observed in the above-mentioned scanning molecule counting method may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. And, in a case that the particle to be observed is a particle which does not emit light, a light-emitting particle is produced by binding a light-emitting probe to the particle to be observed, and thereby, in the above-mentioned light detection, the light of the light-emitting probe bound with the particle to be observed (bound probe) will be detected as the light of the light-emitting particle (For example, see patent document 12). In the preparation of a sample solution in that case, typically, for example, after mixing particles to be observed and light-emitting probes in a solution, the solution is put under a condition promoting the binding reaction of the particles to be observed and light-emitting probes, and thereby, the conjugates of particle to be observed and light-emitting probe, i.e., the light-emitting particles to be the objects to be detected in the Scanning molecule counting method are produced.

In this respect, usually, it is preferable that all the particles to be observed in solution are bound with the light-emitting probes, and therefore, the light-emitting probes will be added into solution so that the number of the light-emitting probes will exceed beyond the number of the particles to be observed. In that case, the light-emitting probes unbound from a particle to be detected (unbound probe) will remain in the solution. However, if there are selected, as the light-emitting probes, probes of a type that emits light when it binds with a particle to be observed but does not emit light substantially when it unbinds from a particle to be observed, the unbound probes are not detected in the light detection procedure even if they exist in the sample solution while only bound probes can be detected selectively. Thus, the light-emitting probes as described above are very advantageous in that the process for removing unbound probes in the sample solution becomes unnecessary. For examples of such light-emitting probes, the types shown in FIGS. 3A-3C are known.

In the case of an example as shown in FIG. 3A, for instance, as a light-emitting probe P, there is employed a molecule having a structure that a fluorescent dye F1 to be an energy donor and a fluorescent dye F2 to be an energy acceptor in an energy transfer phenomenon are bound to the opposite ends of a single strand nucleic acid ss having a particular base sequence (It is known as Molecular beacon.). In this case, in a liberated, single light-emitting probe P (upper left), the energy donor F1 and the energy acceptor F2 are close to one another owing to the flexing and twisting of the single strand nucleic acid ss, and thus, since the energy transfer phenomenon et will arise by irradiating the energy donor F1 with the excitation light, no fluorescence of the energy donor F1 is emitted out (the fluorescence Lf2 of the energy acceptor F2 is emitted.). However, if there exists a nucleic acid T (particle to be observed) which has the base sequence complementary to the base sequence of the single strand nucleic acid ss of the light-emitting probe P, it forms a conjugate with the particle to be observed T (upper right), and thereby, the energy donor F1 and the energy acceptor F2 of the light-emitting probe P separate mutually from one another, so that the fluorescence Lf1 of the energy donor F1 will be emitted out by irradiating the energy donor F1 with the excitation light. That is, in the example of FIG. 3A, only when the light-emitting probe P binds to the particle to be observed T, the fluorescence Lf1 of the energy donor F1 will be emitted out.

Further in the case of an example as shown in FIG. 3B, as a light-emitting probe P, there is employed a molecule having a structure that a fluorescent intercalator F for a double strand nucleic acid is added to the single strand nucleic acid ss which has a particular base sequence. For examples of the fluorescent intercalator molecule, for instance, concretely, Thiazole Orange, Oxazole Yellow, PicoGreen, SYBR Green, SYBR Gold, etc. are raised. In this case, in a liberated, single light-emitting probe P (upper left), the fluorescent intercalator F hardly emits fluorescence, but, if there exists a nucleic acid T (particle to be observed) which has the base sequence complementary to the base sequence of the single strand nucleic acid ss of the light-emitting probe P, it forms double strand nucleic acid (conjugate) with the particle to be observed T (upper right), where the fluorescent intercalator F will be sandwiched between double strand nucleic acid and emit fluorescence Lf.

Furthermore, in the case of an example as shown in FIG. 3C, as a light-emitting probe P, there is employed a set of a probe P1 having a fluorescent dye F1 to be an energy donor in an energy transfer phenomenon and a probe P2 having a fluorescent dye F2 to be an energy acceptor in the energy transfer phenomenon. In in this case, in the condition (upper left) that the probe P1 and the probe P2 are mutually liberated, no energy transfer phenomenon occurs and thus fluorescence Lf2 of the energy acceptor F2 is not emitted even when the energy donor F1 is irradiated with excitation light (fluorescence of the energy donor F1 is emitted.), while, when the probe P1 and the probe P2 bind with a particle to be observed T (upper right), the energy donor F1 and the energy acceptor F2 becomes close to one another, and thus, by irradiating the energy donor F1 with its excitation light, an energy transfer phenomenon et is caused so that fluorescence Lf2 of the energy donor F2 will be emitted.

However, in the case of a light-emitting probe of the type that emits light when it is bound to a particle to be observed and does not emit light substantially when it is unbound from a particle to be observed as illustrated above in FIGS. 3A-3C, even in the condition of an unbound probe, the probe temporarily gets into a light-emitting state because of a stochastic occurrence of an intramolecular structural change, etc. This is because, when a light-emitting probe as described above is unbound from a particle to be observed, in most cases, the stability of its configuration is lower than in the condition that it is bound to a particle to be observed, and thus, stochastic transitions occur between a non-light-emitting state where no light is emitted and a light-emitting state where light is emitted owing to random intramolecular structural changes and motions. In the case of FIG. 3A, for example, as drawn in the lower left of the drawing, when the single strand nucleic acid ss extends straight because of fluctuation of its intramolecular structure, the energy donor F1 and the energy acceptor F2 mutually separate, and thus, by radiating the excitation light for the energy donor F1, fluorescence Lf1 of the energy donor F1 will be emitted. In the case of FIG. 3B, as drawn in the lower left of the drawing, it is possible that the fluorescent intercalator F temporarily bind with a base of the single strand nucleic acid ss of the light-emitting probe P because of fluctuation of its intramolecular structure, and in that case, the fluorescence Lf will be emitted. In the case of FIG. 3C as drawn in the lower left of the drawing, it is possible that the probe P1 and the probe P2 come into a state that they contact mutually during their floating by the Brownian motion, and in that case, by radiating the excitation light for the energy donor F1, the energy transfer phenomenon et occurs so that fluorescence Lf2 of the energy donor F2 will be emitted. Thus, as noted above, when a transition from a non-light-emitting state to a light-emitting state occurs in an unbound probe, an unbound probe also emits the same light as a bound probe until a transition from the light-emitting state to the non-light-emitting state occurs. And in the step of the light detection of Scanning molecule counting method, if an unbound probe being in a temporary light-emitting state is encompassed by the moving light detection region, its light is detected similarly to a bound probe (light-emitting particle), and namely, the unbound probe would be erroneously detected as a light-emitting particle.

In this respect, the period in which an unbound probe will be in a light-emitting state is only from the occurrence of a transition from a non-light-emitting state to a light-emitting state to the occurrence of a transition from the light-emitting state to the non-light-emitting state, and with respect to the period from the transition from the non-light-emitting state to the light-emitting state to the transition from the light-emitting state to the non-light-emitting state, its average time length, i.e., the average lifetime of the light-emitting state, is almost determined, depending upon the kinds of light-emitting probe. Therefore, in the light detection step in the scanning molecule counting method, if the time in which an unbound probe is encompassed by a moving light detection region, i.e., the time for the unbound probe to relatively pass through the inside of the light detection region, is longer than the average lifetime of the light-emitting state of the unbound probe, it becomes possible to discriminate the time variation of light intensity of the unbound probe from the time variations of light intensity of light-emitting particles (bound probes) even when the unbound probe being in the light-emitting state is encompassed by the light detection region.

More in detail, for example, as shown in FIG. 4A, when a light-emitting probe becomes a bound probe BC by binding to a particle to be observed and gets from the non-light-emitting state n-e into the light-emitting state l-e at the time S, after this, the light-emitting state l-e is stably maintained(×1); on the other hand, when a light-emitting probe, remaining in the state of a unbound probe N-BC, gets from the non-light-emitting state n-e into the light-emitting state l-e and remains there only in the average lifetimes $\tau$ (×2), in a case that the width Ts of the time in which the moving light detection region encompasses each of the bound probe BC and unbound probe N-BC is shorter than the average lifetime $\tau$, as shown in FIG. 4B, if the time in which the light detection region encompasses the unbound probe N-BC and the time in which the unbound probe N-BC is in the light-emitting state l-e mutually overlap as illustrated+, the light intensity variation (×4) of the light emitted by the unbound probe N-BC becomes similar to the light intensity variation (×3) of the light emitted by the bound probe BC, and thus, these are not discriminable from each other. However, as shown in FIG. 4C, in a case that the width Ts of the time in which the moving light detection region encompasses each of the bound probe BC and unbound probe N-BC is longer than the average lifetime $\tau$, even if the time in which the light detection region encompasses the unbound probe N-BC and the time in which the unbound probe N-BC is in the light-emitting state l-e mutually overlap, the time in which the unbound probe N-BC is in the non-light-emitting state n-e will almost surely exist within the time in which the light detection region encompasses the unbound probe N-BC. Then, as illustrated, the light intensity variation of the light emitted by the unbound probe N-BC becomes different from the light intensity variation of the light emitted by the bound probe BC, and thus, these becomes discriminable from each other. In this case, concretely, as compared with a case that the light detection region encompasses the bound probe BC, the total amount and time width of the light detected within the time in which the light detection region encompasses the unbound probe N-BC becomes shorter and also, the profile of its light intensity variation becomes different.

Thus, in a case that an unbound probe is one which can temporarily be in a light-emitting state, through adjusting the manner of the moving of a light detection region so as to render the time width in which the light detection region encompasses an unbound probe N-BC to be longer than the average lifetime of the light-emitting state of the unbound probe, erroneous detection of the unbound probe as a bound probe can be avoided or its frequency can be reduced. In this regard, the time width T in which a light detection region encompasses an unbound probe N-BC is determined by the size d in the moving direction of the light detection region and the moving speed of the position of the light detection region, i.e., the scanning rate u, and, concretely, $$T > \tau \qquad (2)$$

is to be established between the time width T and the average lifetime $\tau$ of the light-emitting state of the unbound probe. Here, as noted, light-emitting particles and unbound probes are usually single molecules, molecular aggregates, etc. and these sizes are considered as infinitesimal points relative to the light detection region, and thus, the encompassed time T in a case that a light-emitting probe unbound from a particle to be observed is encompassed by a moving light detection region is the time during which the light detection region moves by a distance equal to the size d in its moving direction, and accordingly, since $$d = uT$$

is established, the scanning speed u of the light detection region is set to be:

$$u < d/\tau. \qquad (3)$$

Furthermore, in the above-mentioned light measurements with moving a light detection region, a more suitable condition is that the total amount of the light detected when the light detection region encompasses an unbound probe N-BC in a light-emitting state is small sufficiently or enough to be effectually ignorable in comparison with the total amount of the light detected when the light detection region encompasses a bound probe BC, so that the light intensity variation of the light emitted by the unbound probe N-BC will not be substantially detected as a signal of a bound probe. In this respect, as noted, in defining the boundary of a light detection region (confocal volume), the intensity of illumination light or excitation light radiated into the inside of the light detection region is regarded to be an effectually ignorable degree when it is reduced to 1/e, and thereby, a surface on which the intensity of illumination light or excitation light is reduced to 1/e is defined as the external surface of the light detection region. Similarly to this, the total amount En of the light detected when a light detection region encompasses an unbound probe N-BC in a light-emitting state can be considered to be small to the effectually ignorable degree if it is less than 1/e of the total amount Ep of the light detected when the light detection region encompasses a bound probe BC, namely, if $$En/Ep<1/e \quad (4)$$

is satisfied. In this connection, since En/Ep is equal to τ/T, the above-mentioned preferable condition, namely, the condition that the light intensity variation of the light emitted by an unbound probe N-BC is not substantially detected as a signal of a bound probe is:

$$T>e\tau. \quad (5)$$

And, the preferable condition for the scanning speed u of the light detection region satisfying Expression (5) is:

$$u<d/(e\tau) \quad (1)$$

(e is the base of natural logarithm.)

Thus, by setting the scanning speed u of the light detection region to satisfy Expression (3) or more preferably Expression (1), the reduction of the frequency or the avoidance of the erroneous detections of unbound probes. In this connection, the average lifetime τ of the light-emitting state of an unbound probe is detectable beforehand by an arbitrary method, and it may be actually measured or a literature value may be used for it. The size d of a light detection region is also detectable beforehand by an arbitrary method.

Operation Processes

In an embodiment of operation processes of an optical analysis in accordance with the present embodiment using the optical analysis device 1 as illustrated in FIG. 1A, basically, the processes described in patent documents 9-13 or described in the other patent applications of the applicant of the present application relating to the scanning molecule counting method may be arbitrarily used. For concrete operation processes, typically, (1) the preparation of a sample solution containing light-emitting particles, (2) the measurement process of the light intensity of the sample solution, and (3) the analysis process of the measured light intensity are carried out. FIG. 5 shows the processes in this embodiment expressed in the form of flow chart. In these processes, as already noted, a light-emitting particle detected in the present embodiment is a conjugate of a particle to be observed and a light-emitting probe, and the light-emitting probe remains stably in a light-emitting state when it is bound to the particle to be observed while a stochastic transition between a non-light-emitting state and a light-emitting state occurs in the light-emitting probe when it is unbound from a particle to be observed, and it is in a light-emitting state for the average lifetime τ when it is unbound from a particle to be observed. Then, the scanning speed of the light detection region is set to satisfy Expression (3) or Expression (1) using the average lifetime τ of the light-emitting state of the light-emitting probe unbound from a particle to be observed.

(1) Preparation of a Sample Solution

In a sample solution, light-emitting probes are distributed or dissolved so that, when particles to be observed exist, their conjugates with light-emitting probes will be formed. Concrete processes of binding light-emitting probes and particles to be observed and preparing the sample solution may be performed appropriately. However, in case of the present embodiment, since light-emitting probes unbound from a particle to be observed may exist in the sample solution, the process for removing the unbound probes is unnecessary. Typically, the sample solution is an aqueous solution, but not limited to this, and it may be an organic solvent or other arbitrary liquids.

(2) Measurement of Light Intensity of a Sample Solution (FIG. 5-Step 100)

The measurement of the light intensity in the optical analysis by the scanning molecule counting method of this embodiment is performed while conducting the moving of the position of the light detection region within the sample solution (the scanning of the inside of the sample solution) by driving the mirror deflector 17 and/or the stage position changing apparatus 17a during the measurement. In the operation processes, typically, after dispensing a sample solution into the well(s) 10 of the micro plate 9 and putting it on the stage of the microscope, when a user inputs to the computer 18 a command of starting the measurement, the computer 18 follows programs (a procedure of moving the position of the light detection region in the sample solution and a procedure of detecting the light from the light detection region during moving the position of the light detection region to generate time series light intensity data) memorized in a memory device (not shown), and then the radiating of excitation light into the light detection region in the sample solution and the measuring of the light intensity are started. During this measurement, under the operational control of the computer 18 according to the program, the mirror deflector 17 and/or the stage position changing apparatus 17a drive the mirror 7 (galvanometer mirror) and/or the micro plate 9 on the stage of the microscope to move the position of the light detection region in the well 10, simultaneously with this, the photodetector 16 successively converts the detected light into electrical signals and transmits them to the computer 18 while the computer 18 generates and saves time series light intensity data from the transmitted signals in an arbitrary manner. In this regard, typically, the photodetector 16 is a super-high sensitive photodetector which can detect an arrival of a single photon, and thus, when the detection of light is conducted by photon counting, the time series light intensity data may be time series photon count data.

The moving speed of the position of the light detection region during the measurement of light intensity (the scanning speed of the light detection region), as noted, may be a predetermined speed set arbitrarily, experimentally or so as to meet the analytic purpose while satisfying Expression (3) or Expression (1) by using the average lifetime τ of the light-emitting state of a light-emitting probe unbound from a particle to be observed. In a case of acquiring the information about the number density or concentration based on the number of the detected light-emitting particles, since the size or volume of the region through which the light detection region passed is needed, the moving of the position of the light detection region is performed in a manner that its moving length is grasped. In this regard, since it is easier to interpret measurement results when the lapsed time during the measurement and the moving length of the position of a light detection region are proportional to one another, it is basically preferable that its moving speed is constant, but not limited thereto.

Further, with respect to the moving speed of the position of the light detection region, in order to perform quantitatively precisely individual detection of light-emitting particles from the measured time series light intensity data or counting of the number of light-emitting particles, it is preferable that the moving speed is set to a value quicker than the moving speed in the random motion, i.e., the Brownian motion of the light-emitting particle. Since light-emitting particles are particles dispersed or dissolved in the solution and moving at random freely, their positions move with time by the Brownian motion. Thus, when the moving speed of the position of the light detection region is slower than the movement of a particle owing to the Brownian motion, the particle moves at random in the region as schematically drawn in FIG. 6A, whereby the light intensity changes at random (as noted, the excitation light intensity in the light detection region is reduced outwardly from the peak at the center of the region), so that it would become difficult to determine a significant light intensity change corresponding to each light-emitting particle. Then, preferably, as drawn in FIG. 6B, the moving speed of the position of the light detection region is set to be quicker than the average moving speed of a particle by the Brownian motion (diffusional moving velocity), so that the particle will cross the light detection region in an approximately straight line and thereby, in the time series light intensity data, as illustrated in FIG. 6C the most upper row, the profile of the change of the light intensity corresponding to each particle will become almost uniform (When a light-emitting particle passes through a light detection region in an approximate straight line, the profile of the change of the light intensity becomes approximately similar to the excitation light intensity distribution.), and thus, the correspondence between each light-emitting particle and light intensity can be easily determined.

Concretely, the time $\Delta t$ required for a light-emitting particle having a diffusion coefficient D to pass through the light detection region of radius Wo (confocal volume) by the Brownian motion is given from the equation of the relation of mean-square displacement:

$$(2Wo)^2 = 6D \cdot \Delta t \tag{6}$$

as:

$$\Delta t = (2Wo)^2/6D \tag{7},$$

and thus, the velocity of the light-emitting particle moving by the Brownian motion (diffusional moving velocity) Vdif, becomes approximately $$\text{Vdif} = 2Wo/\Delta t = 3D/Wo \tag{8}$$

Then, with reference to this Vdif, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $0.3\times10^{-3}$ m/s, supposing Wo is about 2 μm, and therefore, the moving speed of the position of the light detection region may be set to its 2 times or more, 0.6 mm/s, etc. In this regard, when the diffusion coefficient of a light-emitting particle is unknown, an appropriate moving speed of the position of the light detection region may be determined by repeating the execution of a preliminary experiment with setting various moving speeds of the position of the light detection region in order to find the condition that the profile of the light intensity variation becomes an expected profile (typically, similar to the excitation light intensity distribution).

As noted, since the moving speed of the position of the light detection region is set to satisfy Expression (3) or (1), Expression (3) or (1) becomes the condition defining the upper limit of the moving speed of the position of the light detection region. On the other hand, the conditions setting the moving speed of the position of the light detection region to be quicker than the diffusion moving velocity of the light-emitting particle becomes the condition defining the lower limit of the moving speed of the position of the light detection region.

Accordingly, the moving speed u of the position of the light detection region will be set to satisfy the following condition:

$$\text{Vdif} < u < d/\tau \tag{9a}$$

or more preferably, $$\text{Vdif} < u < d/e\tau. \tag{9b}$$

The setting process of the moving speed u of the position of the light detection region may be performed in an appropriate time prior to conducting a light measurement. Concretely, the scanning speed u may be adjusted to a value determined by a user with reference to the value of the average lifetime of the light-emitting state of a light-emitting probe when it is an unbound probe. Or, it may be constructed such that, for plural kinds of molecular species of light-emitting probe, the data of the values of the average lifetimes of the light-emitting state of respective probes being in an unbound state are memorized in a memory apparatus (not shown) of the computer 18, and when a user inputs the molecular species information of a light-emitting probe used for a measurement, the value of the average lifetime corresponding to the input is read out and the computer 18 determines an appropriate moving speed of the position of the light detection region with reference to the value of the average lifetime.

(3) Individual Detection of Signals of Light-Emitting Particles (FIG. 5-Steps 110-160)

When time series light intensity data are generated, the detection of signals of light-emitting particles and the counting of light-emitting particles are performed using light intensity values in time series light intensity data as described in the following. As already noted, when the track of one light-emitting particle in its passing through the light detection region is approximately straight as shown in FIG. 6B, the light intensity variation on the time series light intensity data in the signal corresponding to the particle has a bell shaped profile reflecting the light intensity distribution in the light detection region determined by the optical system (see FIG. 6C, the most upper row). Thus, basically in the scanning molecule counting method, when the time width for which the light intensity value exceeding an appropriately set threshold value continues is in a predetermined range, the signal having the profile of the light intensity may be judged to correspond to one particle having passed through the light detection region, and thereby one light-emitting particle is detected. And a signal, of which the time width for which the light intensity exceeding the threshold value continues is not within the predetermined range, is judged as noise or a signal of a contaminant. Further, when the light intensity distribution in the light detection region can be assumed as a Gaussian distribution:

$$I = A \cdot \exp(-2t^2/a^2) \quad (10),$$

and when the intensity A and the width a, computed by fitting Expression (10) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done. On the other hand, the signal with the intensity A and the width a out of the predetermined ranges may be judged as a noise or a contaminant signal and ignored in the later analysis, etc. In this respect, it is expected that the profiles of the light intensity variations of unbound probes being in the light-emitting state in almost all cases differ from the profile of the approximately bell shape reflecting the light intensity distribution in the inside of the light detection region as illustrated in FIG. 4C, and therefore, it is expected that the lights of unbound probes in the light-emitting state will be judged as noises or contaminant signals.

As one example of more concrete ways for the processes of detection of (a) signal(s) from the time series light intensity data, first, a smoothing treatment is performed to the time series light intensity data (FIG. 6C, the most upper row "detected result (unprocessed)") (FIG. 5 (B)-step 110, FIG. 6C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method. In this regard, parameters in performing the smoothing treatment, e.g., the number of datum points in one time of the averaging, the number of times of moving average executions, etc. in the moving averages method, may be appropriately set so that a data value lack in minute time can be disregarded in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the smoothed light intensity data is computed (step 120). As illustrated in FIG. 6C, the mid-low row "time differential", in the time differential value of time series light intensity data, the value variation increases at the time of the signal value change, and thereby, the start point and the end point of a significant signal can be determined advantageously by referring to the time differential value.

After that, significant pulse signals are detected sequentially on the time light intensity data (Steps 130-160). Concretely, first, on the time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 6C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically a Gauss function as in Expression (10), it may be a Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges, etc. (Step 150). Accordingly, the signal, whose computed parameters of the bell-shaped function are judged to be within the ranges assumed in a light signal corresponding to one light-emitting particle, as shown in FIG. 6D left, is judged as a signal corresponding to one light-emitting particle, and thereby one light-emitting particle has been detected. On the other hand, a pulse signal, whose computed parameters of the bell-shaped function are not within the assumed ranges, as shown in FIG. 6D right, is disregarded as noise. As noted, since the profile of the light intensity variation of an unbound probe in the light-emitting state differs from the profile of the approximately bell shape reflecting the light intensity distribution in the inside of the light detection region, even if the portion of the light intensity variation of the unbound probe in the light-emitting state is recognized as a pulse existing region, it is expected to be judged as a noise or a contaminant signal in the judgment of step 150. In this connection, together with the detection of signals of light-emitting particles, the counting of the number of signals, i.e., the counting of light-emitting particles, may be performed.

The search and judgment of a pulse signal in the process of the above-mentioned steps 130-150 may be repeatedly performed over the whole light intensity data (step 160). In a case that light measurements are performed using excitation lights of mutually different wavelength bands and two or more time series light intensity data are generated corresponding to the excitation lights of the respective wavelength bands, the processes of steps 130-150 may be performed for each time series light intensity data. In this regard, the process for detecting the signal of a light-emitting particle from light intensity data individually may be performed not only in the above-mentioned procedures but in an arbitrary way.

Moreover, in a case that the number of light-emitting particles is determined by counting the number of the signals of the detected light-emitting particles, when the whole volume of the region which the light detection region passed through is further computed in an arbitrary way, the concentration of the light-emitting particle in a sample can be determined from its volume value and the number of light-emitting particles. For example, the whole volume of the region which the light detection region passed through may be determined in a way described in patent documents 9-13.

By the way, in the above-mentioned structure, assuming that the light intensity distribution of excitation light or illumination light in the inside of the light detection region has a bell shaped profile, and thus, in the detection of the signal of a light-emitting particle, the fitting of a bell type function, such as a Gauss function, to the pulse form, significant increase of light intensity in time series light intensity data is performed; however, in a case that the profile of the light intensity distribution of excitation light or illumination light in the inside of the light detection region does not have a bell shape, a function possessing a profile which matches the profile of the light intensity distribution may be used for the fitting for the detection of the signal of a light-emitting particle. For instance, when the profile of the light intensity distribution of the excitation light or illumination light in the inside of the light detection region is trapezoidal or rectangular, a function matching this shape is used for the above-mentioned fitting process, and then, parameters, such as the maximum intensity Ipeak, the full width at half maximum Wpeak, the correlation coefficient, etc. in the fitting are computed out, and the pulse signal whose computed parameters of the function are within ranges assumed in a signal corresponding to one light-emitting particle is judged as a signal of a light-emitting particle.

In order to verify the validity of the present embodiment explained above, the experiments described below were conducted. In this regard, it should be understood that the following embodiments illustrate the validity of the present embodiment only, not intended to limit the scope of the present invention.

Embodiment 1

Detection of Nucleic Acid Using Molecular Beacon

Using a single strand nucleic acid molecule of a specific base sequence as a particle to be observed, and using a molecular beacon as a light-emitting probe, a conjugate of the particle to be observed and the molecular beacon was detected as a light-emitting particle according to the scanning molecule counting method of the present embodiment. The molecular beacon is a nucleic acid molecule in which a donor dye and an acceptor dye are attached to the opposite ends, respectively, as explained in relation to FIG. 3A, and this molecule is constructed such that a fluorescence energy transfer phenomenon from the donor dye to the acceptor dye occur in its single free form because the donor dye and acceptor dye are close to one another while no fluorescence energy transfer phenomenon can occur when it binds to a nucleic acid or a nucleic acid analogue having a base sequence complementary to its own base sequence because the distance between the donor dye and the acceptor dye becomes long.

In the experiment, as the molecular beacon, a nucleic acid having the following base sequence and being attached with ATTO647N (donor dye) at 5' end, and with BHQ3 (acceptor dye; however, in this case, fluorescence is rarely emitted) at 3' end was used.

ATTO647N-
cctacgccaacagctccaactacgtagg-BHQ3

And, a nucleic acid having the following base sequence was used for the particle to be observed (expressed as TRG, hereafter).

tgactgaatataaacttgtggtagttggagctggtggcgtaggca

The molecular beacon (expressed as MB, hereafter.) has self-complementary sequences in the last 6 base ends. In this regard, the above-mentioned nucleic acids were compounded by requesting Sigma genosis, Inc.

In preparing sample solutions, there were prepared a solution in which MB and TRG were dissolved in a buffer solution (10 mM Tris-HCl, 200 mM NaCl, 0.05% Triton-X100) to be 1 pM MB and 100 nM TRG, and a control solution containing no TRG. Then, the prepared solutions were maintained for 10 seconds at 95° C. using a thermal cycler (made by MJ, PTC-200), causing denaturation of the nucleic acids, and after this, by lowering their temperature to 35° C. at 1° C./minute in rate, the hybridization reaction of MB and TRG was caused. In this regard, in the present embodiment, since it was aimed at comparing the results of the condition in which MB was bound to TRG, i.e., the condition of a bound probe and the condition that MB existed alone, i.e., the condition of a unbound probe, TRG was superfluously mixed relative to MB so that all the MB(s) would form a conjugate with TRG in the solution containing MB and TRG (differing from a usual case for detecting a particle to be observed).

In the light measurement in accordance with the method of the present embodiment, for an optical analysis device, single molecule-fluorescence measuring device MF-20 equipped with the optical system of a confocal fluorescence microscope and a photon counting system (Olympus Corporation) was used, and according to the manner explained in the above-mentioned "(2) Measurement of Light Intensity of a Sample Solution", time series photon count data were acquired for each of the above-mentioned sample solutions. In that time, laser light of 633 nm was used for excitation light, and the detected light wavelength was set to be from 660 to 770 nm using a band pass filter. The moving speed of the position of the light detection region in the sample solution was variously changed in 100-12000 rpm (0.75-90 mm/sec.), and BIN TIME was set to 10 microseconds and the measuring time was set to 20 seconds. After the light intensity measurement, according to the procedure described in the above-mentioned "(3) Individual detection of signals of light-emitting particles", light signals detected in time series data from the time series photon count data, acquired for each sample solution were counted. In smoothing the data by the moving average method in step 110, Savitzky-Golay method was used, wherein 11 data points were averaged at once and the moving average process was repeated 5 times. Further, in the fitting of step 140, a Gauss function was fit to time series data by a least-squares method, determining a peak intensity, a pulse width (full width at half maximum), a correlation coefficient (in the Gauss function). Furthermore, in the judgment process in step 150, only a pulse signal satisfying the following conditions:

20 μsecond<pulse width<200 μsecond

Peak intensity>1(a photon/10 μsecond)

Correlation coefficient>0.95 (A)

was judged as a signal corresponding to a light-emitting particle while pulse signals which did not satisfy the above-mentioned conditions were disregarded as noises, and the number of the signals judged as a light signal corresponding to a light-emitting particle was counted as the particle count.

FIG. 7A shows the numbers of signals, detected as a signal of a light-emitting particle (detected particle count), in the sample solution (PC) containing MB and TRG and the control solution (NC) containing only MB, respectively, in the cases that light measurements were performed at various scanning speeds of the light detection region. The values are the detected numbers in the light measurements performed for 20 seconds. In this connection, it is considered that, in PC, substantially all MB(s) were in the condition that each forms a conjugate with a TRG while, in NC, all MB(s) were in the condition that each exists in the liberated form. Thus, with reference to the drawing, while the detected particle counts increased in both the PC and the NC together with the increase of the scanning speed (this was because the scanning volume increased with the scanning speed), the ratio of the difference in the detected particle counts between PC and NC relative to the detected particle counts increased as the scanning speed was lower. FIG. 7B is a drawing showing the above-mentioned results which were converted into the ratios of the detected particle count of PC to the detected particle count of NC (Signal to Noise ratio). In this regard, for comparison, the ratios of light intensities in the light measurements (the ratios of the light intensity in PC to the light intensity in NC) are shown together. As understood from the drawing, with reference to the ratios of light intensities, irrespective of the scanning speed, the light intensity generally increased under the existence of TRG, and thereby it is understood that the fluorescence intensity increased owing to the binding of MB to TRG. On the other hand, with reference to the signal to noise ratios of detected particle counts, it is understood that, when the scanning speed was lower than the speed at which the time for the light detection region to encompass a light-emitting particle exceeds beyond 200 μseconds, the signal to noise ratio of the detected particle counts increased drastically. Since the signal to noise ratio of detected particle counts becomes higher as the frequency of erroneous detection of an unbound probes as a bound probe becomes lower, the above-mentioned result shows that the frequency of erroneous detection of an unbound probe as a bound probe is reduced if the time for the light detection region to encompass a light-emitting particle exceeds beyond 200 μseconds.

By the way, with respect to MB used in the present embodiment, according to the non-patent document 1, in MB, the rate constant, kopen, of the transition from the condition that a single strand nucleic acid is bent while the opposite ends are close to each other (the non-light-emitting state) to the condition that the single strand nucleic acid extends straight while the opposite ends are separated apart (the light-emitting state) is 2000 to 3000 [1/second], and the rate constant, kclose, of the transition from the condition that the single strand nucleic acid extends straight while the opposite ends are separated apart (the light-emitting state) to the condition that the single strand nucleic acid is bent while the opposite ends are close to each other (the non-light-emitting state) is 5000 to 40000 [1/second]. From these values, the average lifetime of the light-emitting state of an unbound probe will be estimated to be 25 to 200 μseconds. On the other hand, as noted above, in the result of FIG. 7B of Embodiment 1, since the signal to noise ratio increased when the time for the light detection region to encompass a light-emitting particle exceeded beyond 200 μseconds corresponding to the average lifetime of the light-emitting state of an unbound probe, this increase of the signal to noise ratio suggests that, as understood from the explanation related to FIGS. 4A-4C, when the time for the light detection region to encompass a light-emitting particle becomes longer than the average lifetime of the light-emitting state of an unbound probe, a light intensity variation owing to an unbound probe is not recognized as a pulse signal (disappearance of the intensity increase by the smoothing process), or a light intensity variation owing to an unbound probe, even if recognized as a pulse signal, does not satisfy the judgment condition of the signal of a light-emitting particle, and thereby it is hard to be judged as a signal of a light-emitting particle. That is, the above-mentioned results suggest that, according to the teaching of the present invention, by setting the scanning speed of a light detection region so that the time for the light detection region to encompass an unbound probe will be longer than the average lifetime of the light-emitting state of the unbound probe, the possibility of erroneous detection of the unbound probe as a bound probe will be reduced sharply, and the detection precision of a bound probe, i.e., the signal of a light-emitting particle, will be improved.

SEQUENCE LISTING

15P01641.ST25.txt

The invention claimed is:

1. An optical analysis method of detecting light from light-emitting particles substantially uniformly dispersed and moving at random in a sample solution using an optical system of a confocal microscope or a multiphoton microscope, comprising:
   (a) moving a position of a light detection region of the optical system in the sample solution;
   (b) measuring a light intensity from the light detection region during the moving of the position of the light detection region in the sample solution to generate time series light intensity data;
   (c) detecting individually each of signals of the light-emitting particles on the time series light intensity data; and
   (d) counting the number of the signals of the light-emitting particles detected individually to determine a concentration of the light-emitting particles in the sample solution based on the number;
   wherein the light-emitting particles are particles formed by binding a particle to be observed with a light-emitting probe which emits light in a wavelength band of the detected light by being bound to the particle to be observed,
   wherein when the light-emitting probe is unbound from a particle to be observed, the unbound Eight-emitting probe undergoes a stochastic transition between a non-light-emitting state where no light is substantially emitted in the wavelength band of the detected light and a temporary light-emitting state where the unbound light-emitting probe has a molecular structure causing light to be temporarily emitted in the wavelength band of the detected light,
   and wherein the step of moving the position of the light detection region comprises a step of adjusting a moving speed of the position of the light detection region to make an encompassing time during which the unbound light-emitting probe unbound is encompassed by the moving light detection region longer than an average lifetime, which represents a length of time during which the unbound light-emitting probe is in the temporary light-emitting state, so that the unbound light-emitting probe in the temporary light-emitting state is substantially undetected.

2. The method of claim 1, wherein the moving speed of the position of the light detection region is determined based on molecular species information of the light-emitting probe.

3. The method of claim 1, wherein the moving speed u of the position of the light detection region is set smaller than a value obtained by dividing a size d of the light detection region in its moving direction by an average lifetime $\tau$ of the light-emitting probe.

4. The method of claim 3, wherein the moving speed u of the position of the light detection region is set to satisfy a conditional expression using the base of natural logarithm e:

$$u < d/(e\tau).$$

5. The method of claim 1, wherein the light-emitting probe is a molecule from which emitted light intensity changes with an intramolecular structural change, and, in the step (c), the signal from each of the light-emitting particles is detected individually by detecting individually, as a signal of one light-emitting particle, a time variation of the light intensity in the time series light intensity data which has a profile assumed in the light from one light-emitting particle which moves relatively the inside of the light detection region.

6. The method of claim 1, wherein the light-emitting probe is a probe formed by an intercalator fluorescent molecule binding to a nucleic acid, and, in the step (c), the signal from each of the light-emitting particles is detected individually by detecting individually, as a signal of one light-emitting particle, a time variation of the light intensity in the time series light intensity data which has a profile assumed in the light from one light-emitting particle which moves relatively the inside of the light detection region.

7. The method of claim 1, wherein the light-emitting probe includes a first probe to be an energy donor in a fluorescence energy transfer phenomenon and a second probe to be energy acceptor in the fluorescence energy transfer phenomenon while the detected light is light of the second probe emitted through the fluorescence energy transfer phenomenon occurring in a condition that both the first and second probes are bound to the particle, and, in the step (c), the signal from each of the light-emitting particles is detected individually by detecting individually, as a signal of one light-emitting particle, a time variation of the light intensity in the time series light intensity data which has a profile assumed in the light from one light-emitting particle which moves relatively the inside of the light detection region.

8. The method of claim 1, wherein, in the step (a), the position of the light detection region is moved at a speed quicker than the diffusion moving velocity of the light-emitting particle.

9. An optical analysis device which detects light from light-emitting particles dispersed and moving at random in a sample solution using an optical system of a confocal microscope or a multiphoton microscope, comprising:
   a light detection region moving portion which relatively moves a position of a light detection region of the optical system in the sample solution;
   a light detecting portion which detects light from the light detection region; and
   a signal processing portion which generates time series light intensity data of the light from the light detection region detected with the light detecting portion during the moving of the position of the light detection region in the sample solution and detects each of signals of the light-emitting particles individually in the time series light intensity data;
   wherein the light-emitting particles are particles formed by binding a particle to be observed with a light-emitting probe which emits light in a wavelength band of the detected light by being bound to the particle to be observed, and
   wherein when the light-emitting probe is unbound from a particle to be observed, the unbound light-emitting probe undergoes a stochastic transition between a non-light-emitting state where no light is substantially emitted in the wavelength band of the detected light and a temporary light-emitting state where the unbound light-emitting probe has a molecular structure causing light to be temporarily emitted in the wavelength band of the detected light;
   and wherein a moving speed of the position of the light detection region moved by the light detection region moving portion is set to make an encompassing time during which the unbound light-emitting probe is encompassed by the moving light detection region longer than an average lifetime, which represents a length of time during which the unbound light-emitting probe is in the temporary light-emitting state, so that the unbound light-emitting probe in the temporary light-emitting state is substantially undetected.

\* \* \* \* \*